US008652188B2

(12) United States Patent
Hamada et al.

(10) Patent No.: US 8,652,188 B2
(45) Date of Patent: Feb. 18, 2014

(54) LIGHT IRRADIATION DEVICE

(75) Inventors: Chosei Hamada, Kadoma (JP); Masako Yamasaki, Akashi (JP); Takashi Matsuzaki, Shimane (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/142,635

(22) PCT Filed: Jan. 8, 2010

(86) PCT No.: PCT/JP2010/050175
§ 371 (c)(1),
(2), (4) Date: Jun. 29, 2011

(87) PCT Pub. No.: WO2010/079834
PCT Pub. Date: Jul. 15, 2010

(65) Prior Publication Data
US 2011/0270365 A1     Nov. 3, 2011

(30) Foreign Application Priority Data
Jan. 8, 2009     (JP) .................................. 2009-002762

(51) Int. Cl.
*A61N 5/06*     (2006.01)
(52) U.S. Cl.
USPC ...................... 607/89; 606/9; 607/88; 607/90
(58) Field of Classification Search
USPC ..................................... 606/9; 607/88, 89, 90
See application file for complete search history.

(56) References Cited

U.S. PATENT DOCUMENTS

| 5,683,380 A | 11/1997 | Eckhouse et al. |
| 5,885,273 A | 3/1999 | Eckhouse et al. |
| 6,168,590 B1 * | 1/2001 | Neev .................................. 606/9 |
| 2004/0230260 A1 | 11/2004 | MacFarland et al. |
| 2006/0004347 A1 * | 1/2006 | Altshuler et al. ................. 606/4 |
| 2007/0239144 A1 | 10/2007 | Korenberg |
| 2010/0131035 A1 | 5/2010 | Hamada et al. |
| 2010/0152719 A1 | 6/2010 | Fujikawa |

FOREIGN PATENT DOCUMENTS

| EP | 0736308 | 10/1996 |
| JP | 2004-321401 | 11/2004 |
| JP | 2005-080747 | 3/2005 |
| JP | 2005-211689 | 8/2005 |
| JP | 2007-252945 | 10/2007 |
| JP | 2008-289809 | 12/2008 |
| JP | 2008-289812 | 12/2008 |
| JP | 2009-532079 | 9/2009 |

(Continued)

OTHER PUBLICATIONS

Japanese office action dated Jun. 9, 2009.

(Continued)

*Primary Examiner* — Bill Thomson
*Assistant Examiner* — Jeffrey Lipitz
(74) *Attorney, Agent, or Firm* — Greenblum & Bernstein, P.L.C.

(57) ABSTRACT

To provide a light irradiation device capable of easily removing and reducing hair with low power light without burden on skin. The light irradiation device according to the present invention includes a light source giving pulses of light in a wavelength range from 400 to 1200 nm and a light guide distributing the pulses of light given from the light source with energy intensity of 0.2 to 10 J/cm² at a predetermined distance from the light outgoing surface.

3 Claims, 18 Drawing Sheets

(56) References Cited

FOREIGN PATENT DOCUMENTS

| | | |
|---|---|---|
| RU | 2294223 | 2/2007 |
| WO | 2007/106339 | 9/2007 |
| WO | 2008/129740 | 10/2008 |
| WO | 2008/146789 | 12/2008 |

OTHER PUBLICATIONS

Search report from E.P.O., mail date is Apr. 24, 2012.
Russian Office Action dated Aug. 28, 2012, and English translation thereof.
Korean Office Action dated Oct. 19, 2012.
Japan Office action, mail date is Feb. 12, 2013.

* cited by examiner

FIG. 16
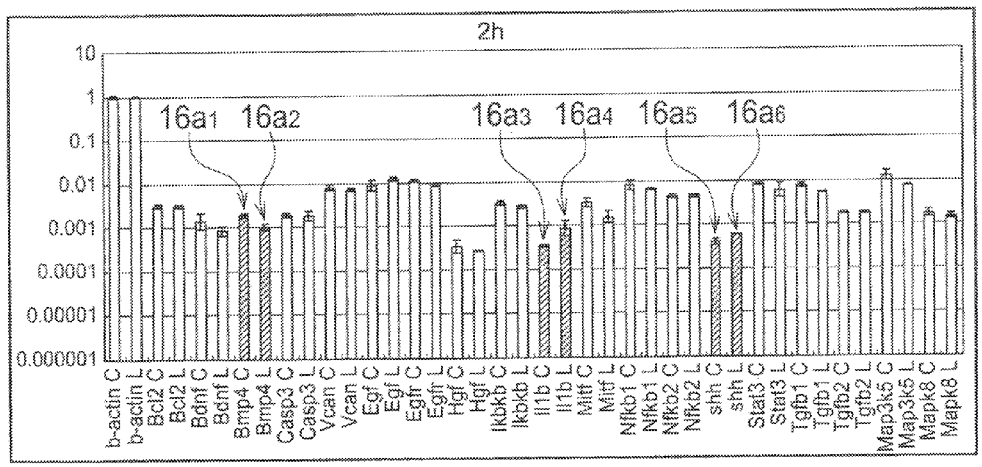
(a)
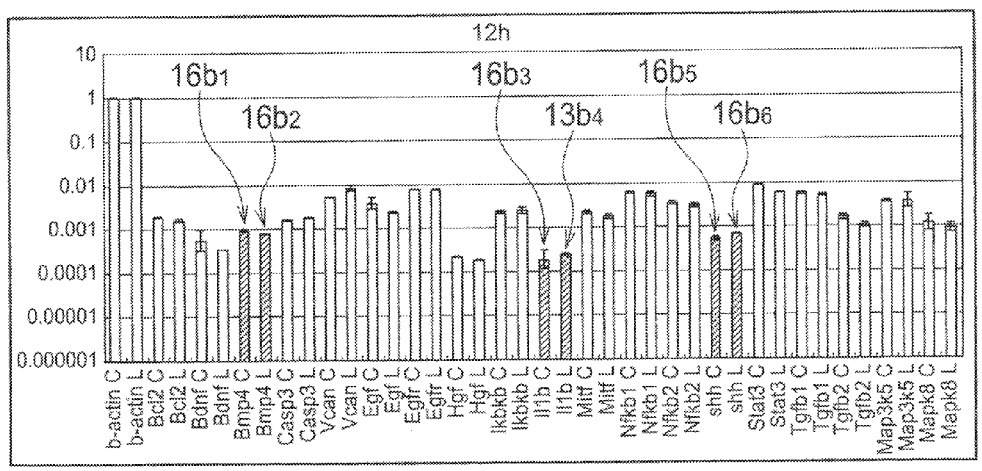
(b)
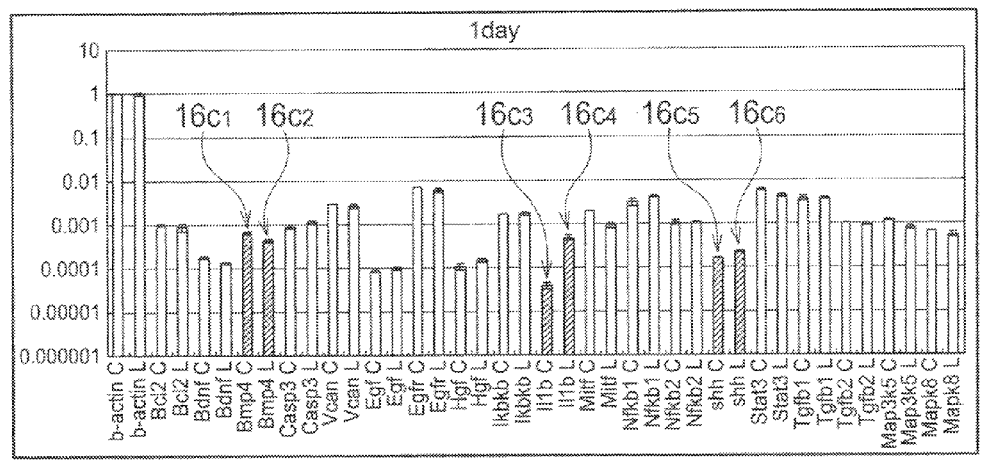
(c)

FIG. 18
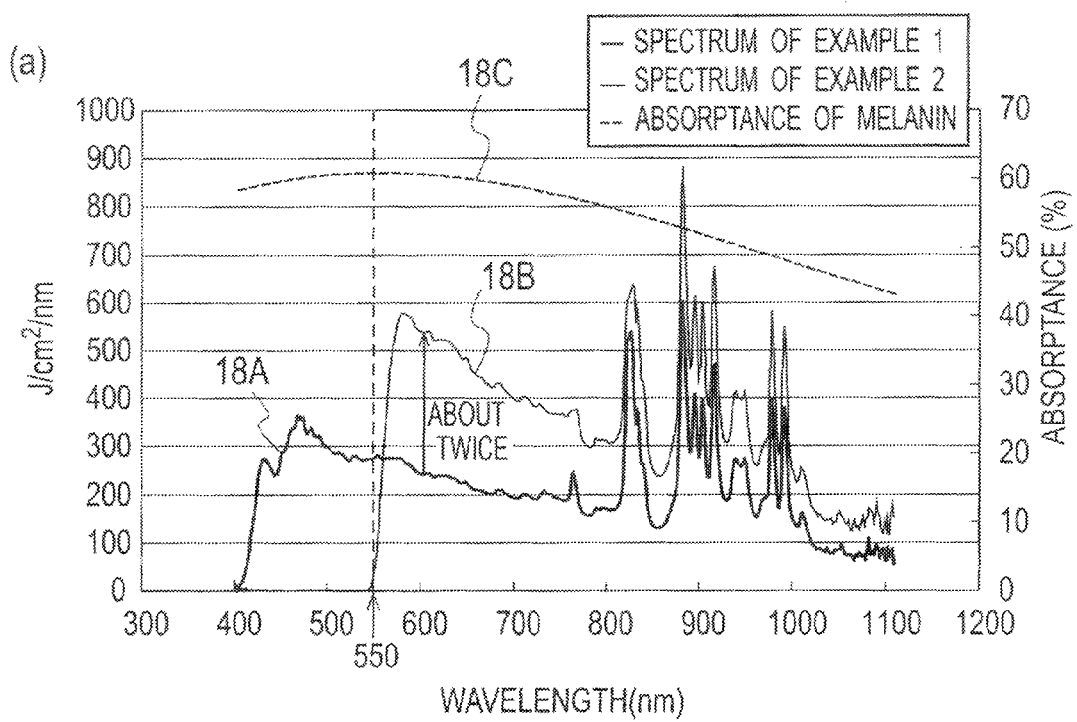
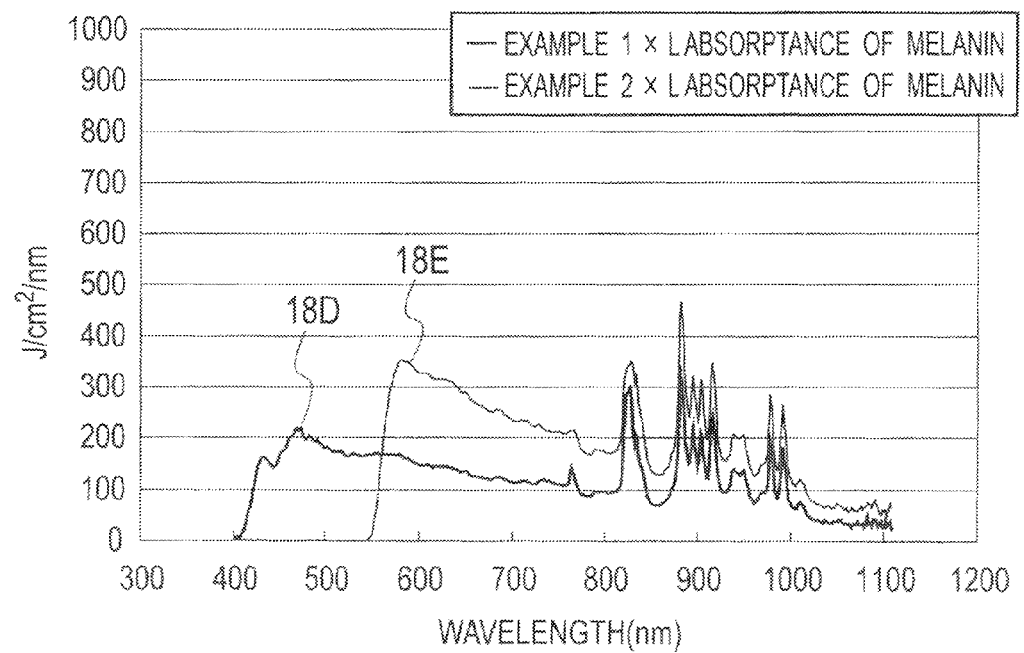

FIG. 19
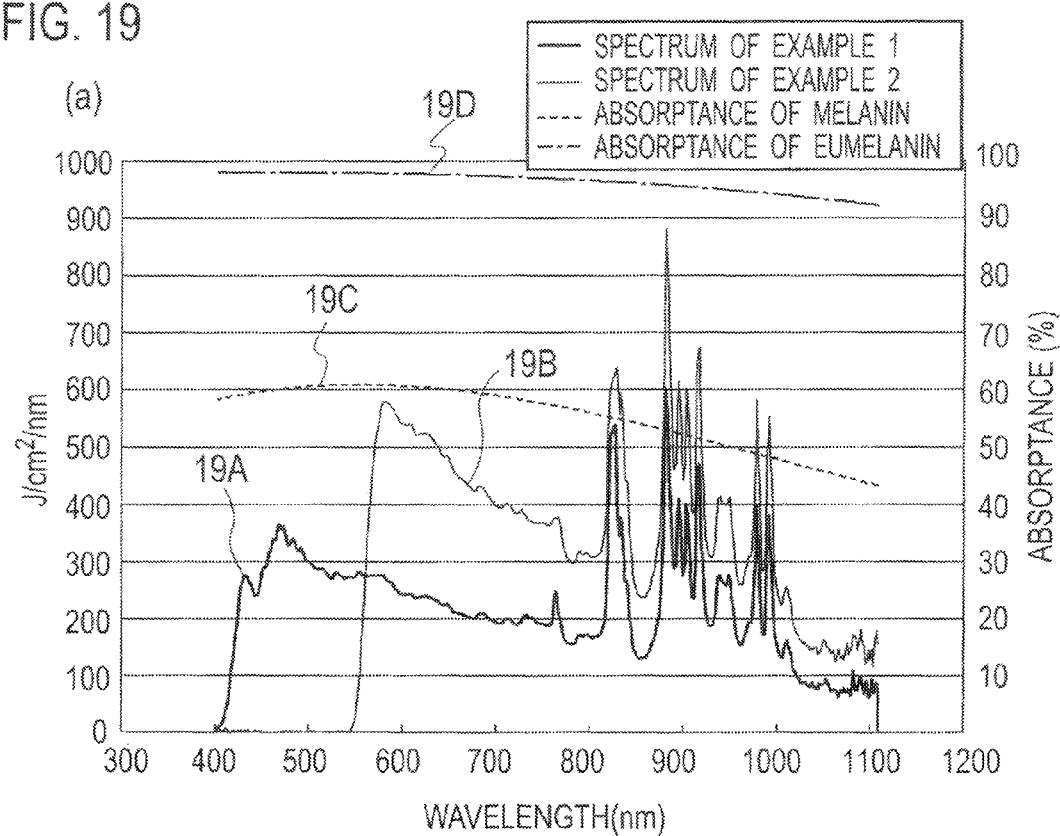
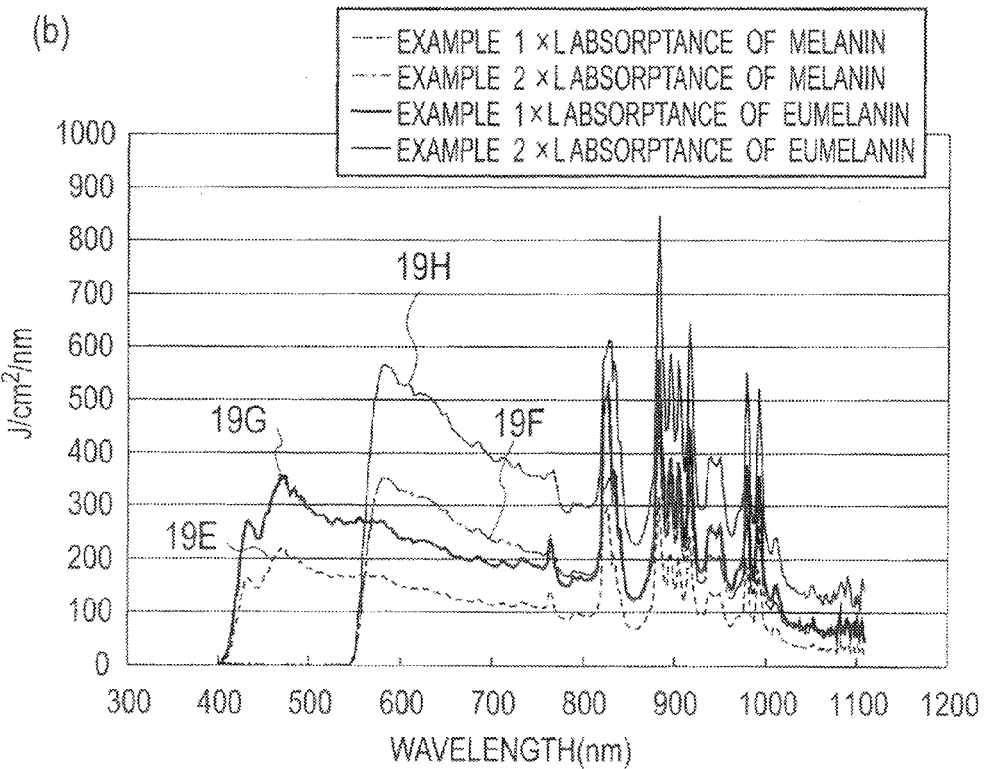

# LIGHT IRRADIATION DEVICE

TECHNICAL FIELD

The present invention relates to a light irradiation device performing light irradiation for hair removal or reduction.

BACKGROUND ART

In the medical field, hair removal or reduction by light irradiation is known. Hair is removed or reduced by irradiating skin with high power laser light (class 4) to cause necrosis of cells of hair roots and follicles. Such hair removal or reduction using laser light is accompanied with destruction of cells and tends to cause side effects such as burns or freckles, thus giving large burden to skin. The operations are therefore conducted by expert doctors. However, the operations by expert doctors cause economical and temporal burdens. Accordingly, there are demands for hair removal or reduction equipment capable of being easily used at home. For example, JP 2005-211689 A discloses a home hair removal device projecting low power light.

CITATION LIST

Patent Literature

Patent Literature 1: JP 2005-211689 A

SUMMARY OF INVENTION

Technical Problem

However, conventional home removal devices only promote denaturation of protein, and cells do not die and remain alive. Thus the conventional home removal devices cannot provide sufficient hair removal or reduction effect.

Solution to Problem

The present invention was made to solve the aforementioned problem, and a light irradiation device according to the present invention includes: a light source giving pulses of light in a wavelength range from 400 to 1200 nm; and a light guide distributing the pulses of light given from the light source with energy intensity of 0.2 to 10 $J/cm^2$ at a predetermined distance from the light outgoing surface. The light guide includes a light orientation controller adjusting the pulses of light from the light source.

Advantageous Effects of Invention

According to the present invention, it is possible to provide a light irradiation device capable of easily removing or reducing hair by projecting low-power light to stop cell proliferation of hair follicles or induce cellular death (apoptosis) without giving burden on skin.

BRIEF DESCRIPTION OF THE DRAWINGS

FIG. 16(a) is a diagram illustrating a result of real time PCR two hours after irradiation, FIG. 16(b) is a diagram illustrating a result of real time PCR 12 hours after irradiation, and FIG. 16(c) is a diagram illustrating a result of real time PCR a day after irradiation.

FIG. 18(a) is a diagram illustrating irradiation spectra of Examples 1 and 2 and melanin absorptance, and FIG. 18(b) is a diagram illustrating a comparison of energies absorbed by melanin in Examples 1 and 2, the absorbed energies are calculated by multiplying the irradiation spectra of Examples 1 and 2 by the melanin absorptance.

FIG. 19(a) is a diagram illustrating irradiation spectra of Examples 1 and 2, melanin absorptance, and eumelanin absorptance, FIG. 19(b) is a diagram illustrating a comparison between energies absorbed by melanin and eumelanin in Examples 1 and 2, the absorbed energies are calculated by multiplying the irradiation spectra of Examples 1 and 2 by the melanin absorptance and eumelanin absorptance.

DESCRIPTION OF EMBODIMENTS

Figure 1:
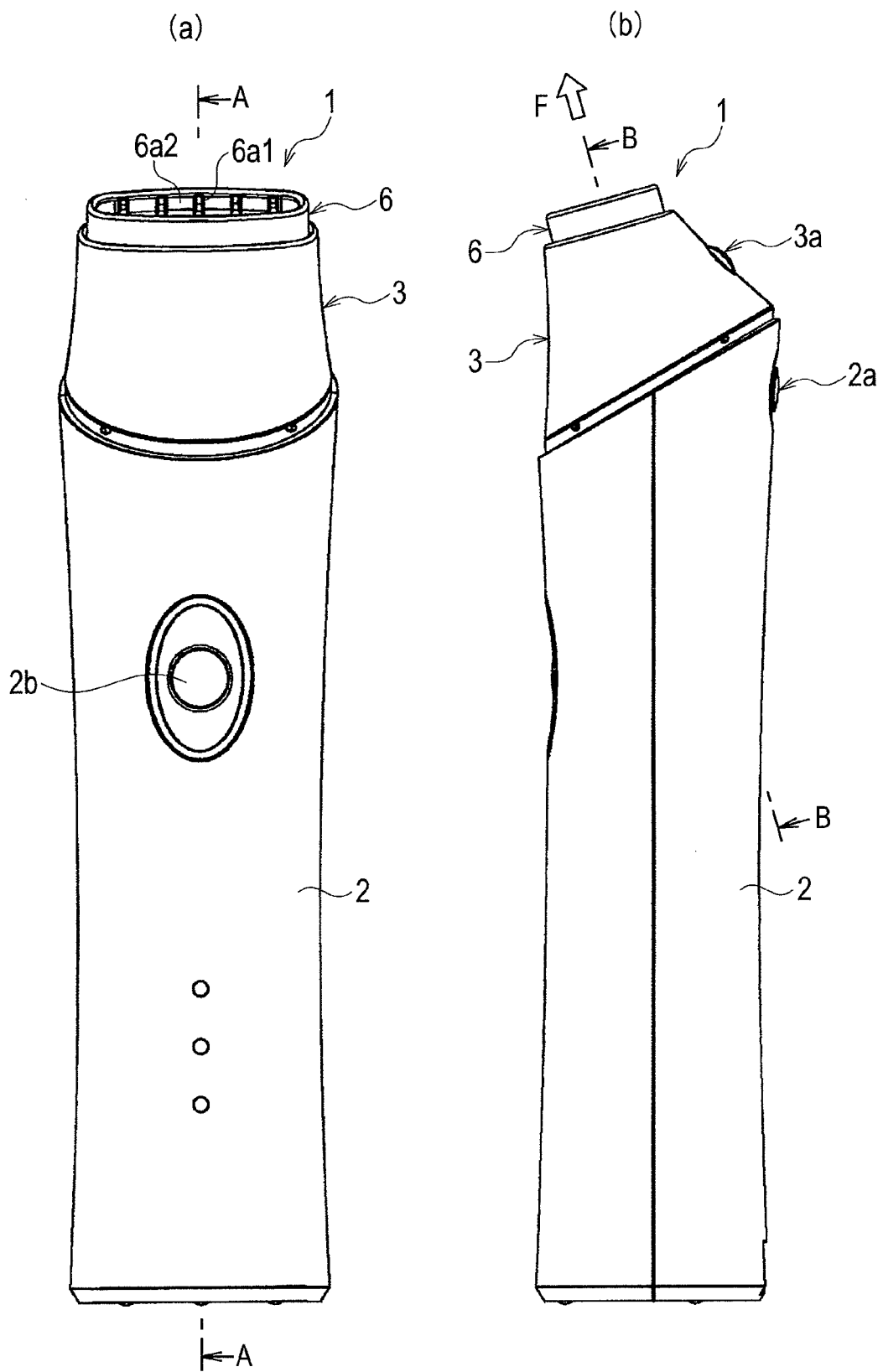
FIG. 1(a) is a front view illustrating an appearance of a light irradiation device according to one embodiment of the present invention.
FIG. 1(b) is a side view illustrating the appearance of the light irradiation device according to the embodiment of the present invention.
Figure 2:
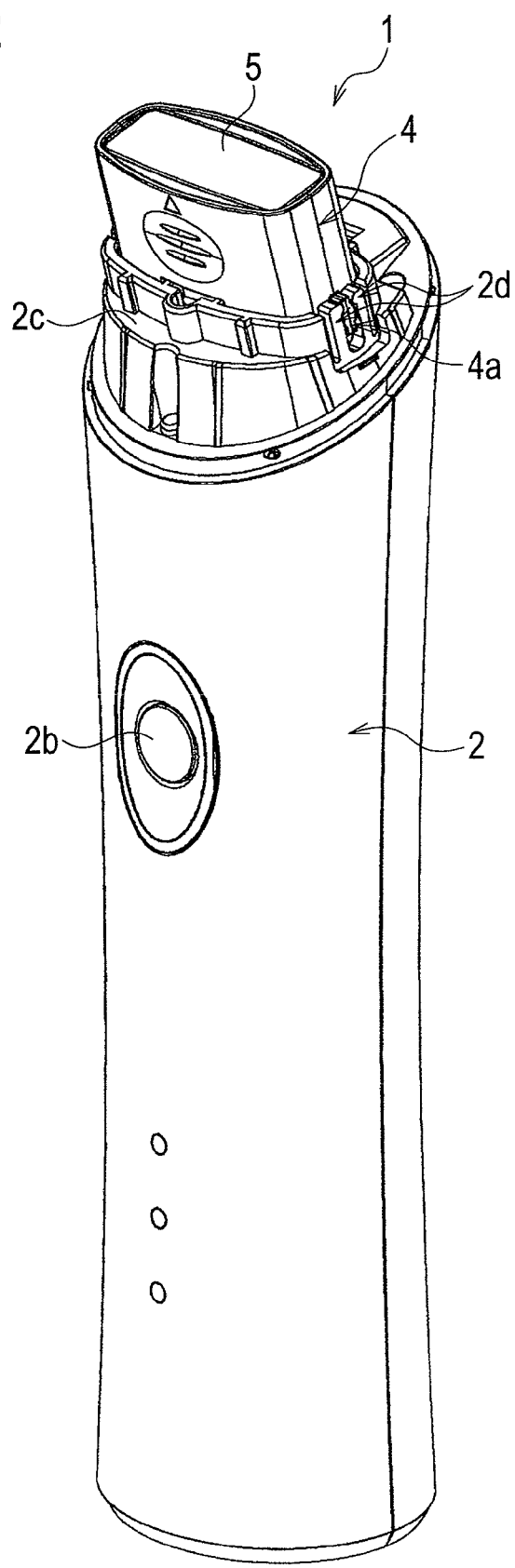
FIG. 2 is a perspective view of the light irradiation device with a light orientation controller and a body cover removed.
Figure 3:
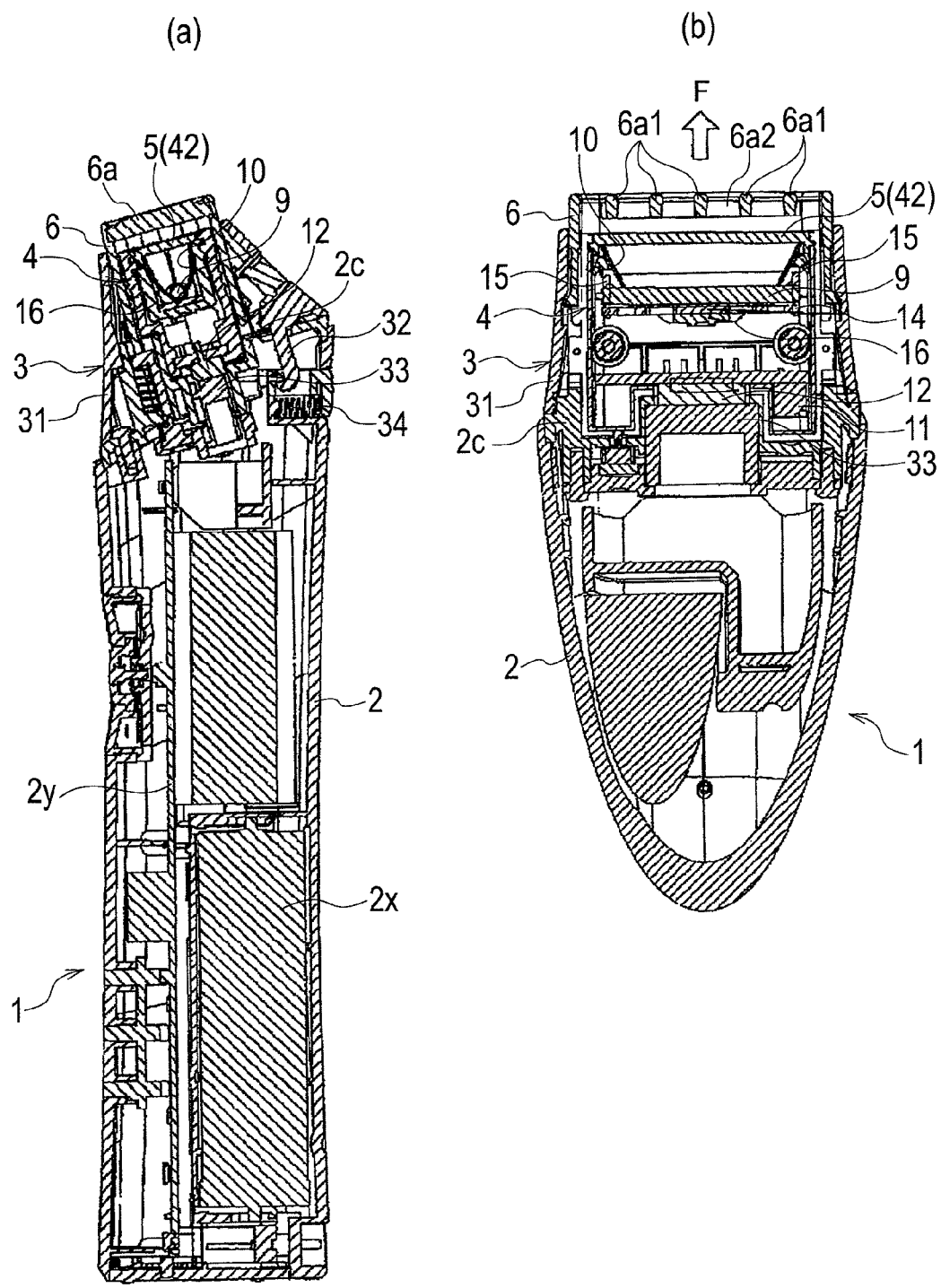
FIG. 3(a) is a cross-sectional view taken along a line A-A of FIG. 1(a)
FIG. 3(b) is a cross-sectional view taken along a line B-B of FIG. 1(b).
Figure 4:
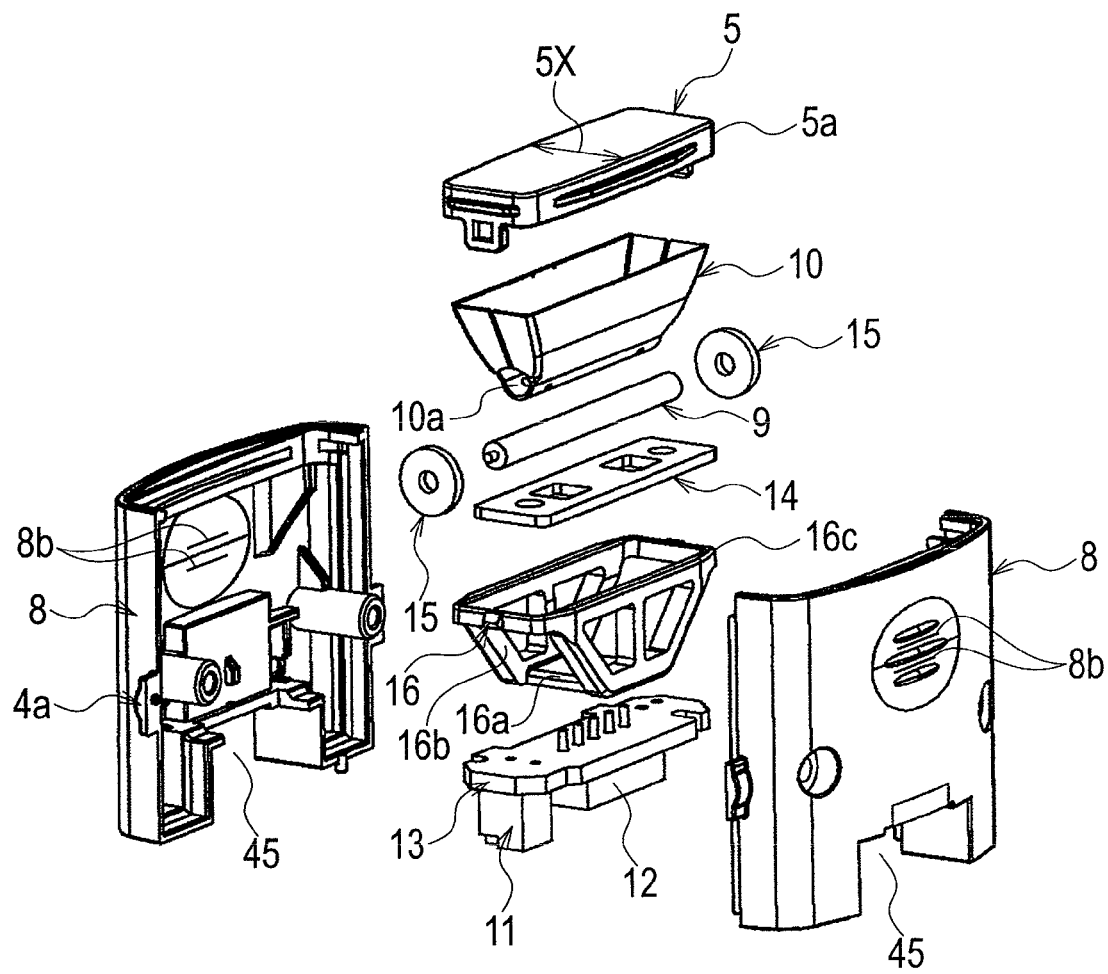
FIG. 4 is an exploded perspective view of an irradiation unit.
Figure 5:
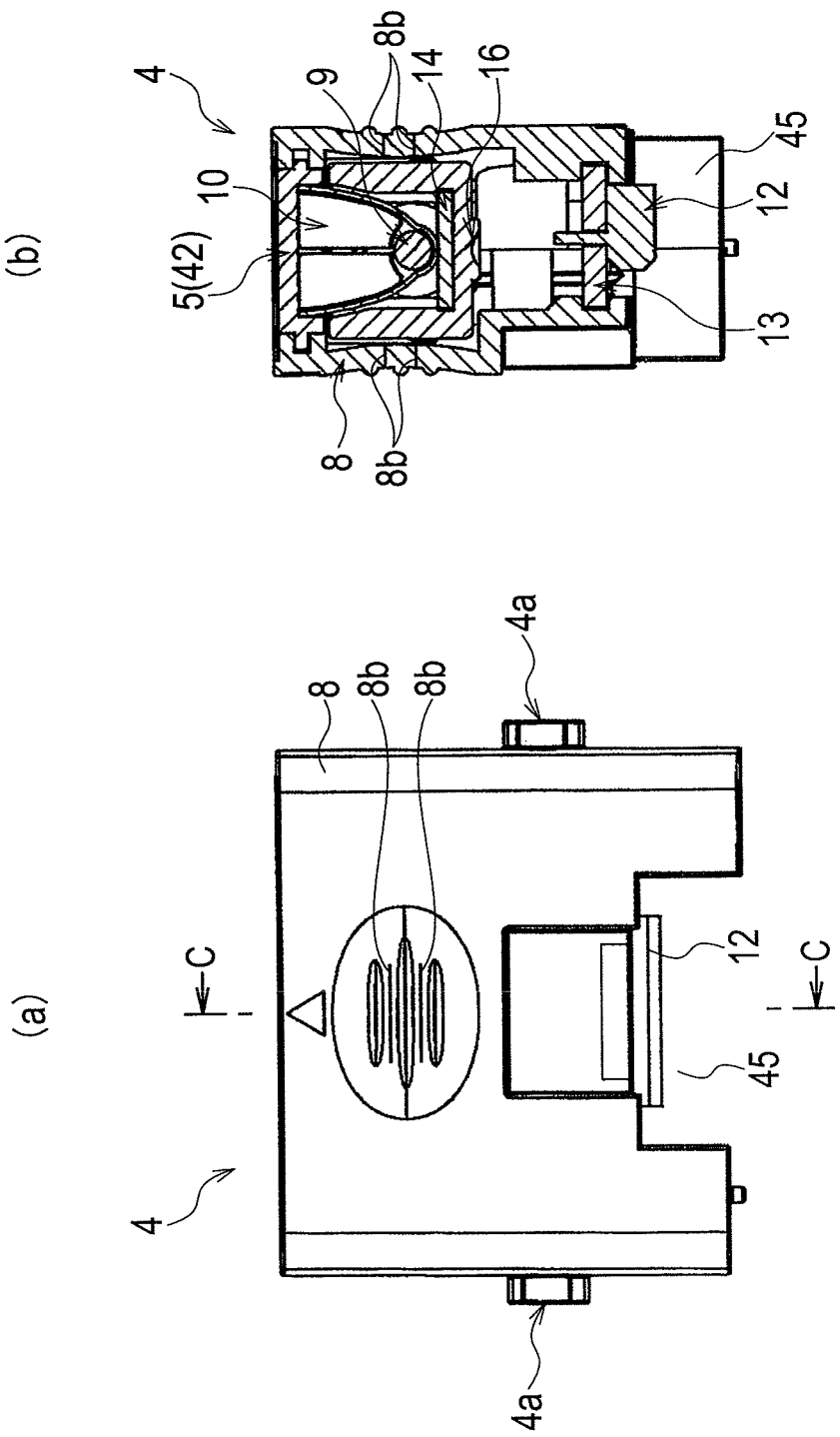
FIG. 5(a) is a front view illustrating the irradiation unit.
FIG. 5(b) is a cross-sectional view taken along a line C-C of FIG. 5(a).
Figure 6:
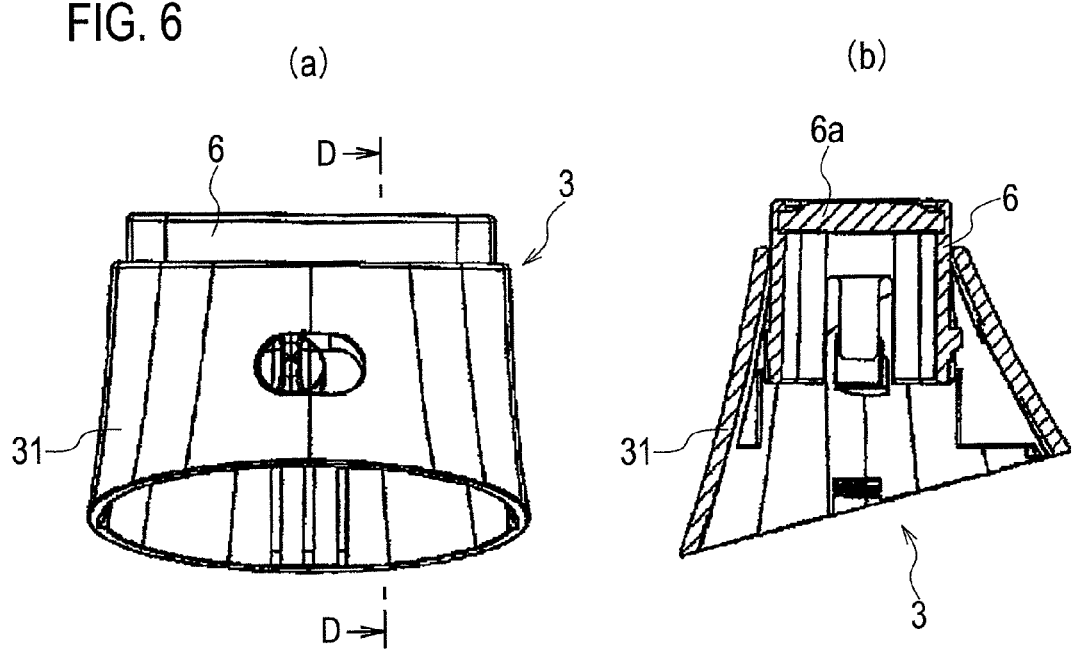
FIG. 6(a) is a front view illustrating the light orientation controller and body cover.
FIG. 6(b) is a cross-sectional view taken along a line D-D of FIG. 6(a).
Figure 7:
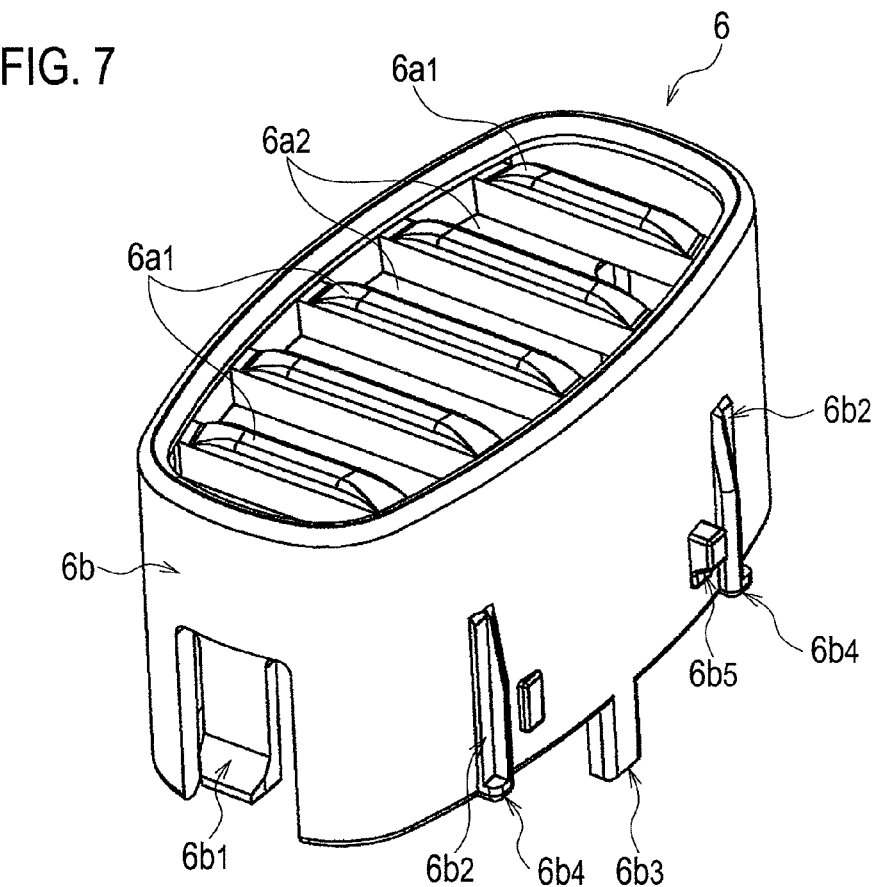
FIG. 7 is a perspective view of the irradiation unit.
Figure 8:
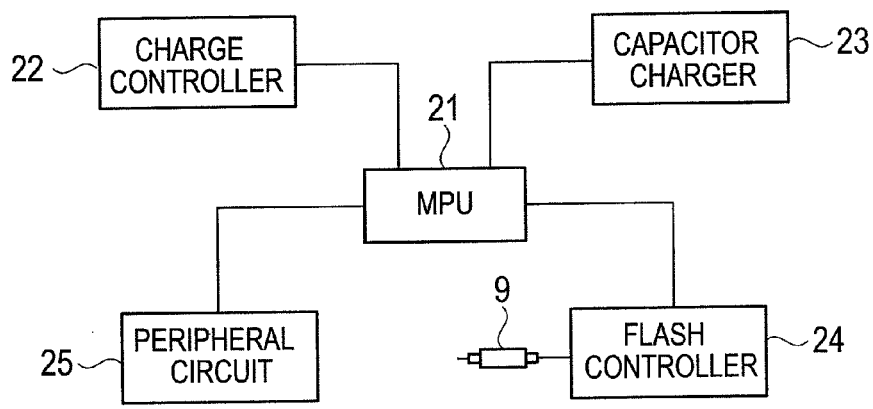
FIG. 8 is a block diagram of a control circuit provided within the body and light orientation controller.

Hereinafter, a description is given of a light irradiation device according to the present invention based on one embodiment illustrated in the accompanying drawings. FIGS. 1(a) and 1(b) are front and side views illustrating an appearance of a light irradiation device 1 according to the embodiment of the present invention, respectively. FIG. 2 is a perspective view of the light irradiation device 1 illustrated in FIGS. 1(a) and 1(b) with a light orientation controller 6 and a body cover 3 removed. FIGS. 3(a) and 3(b) are cross-sectional views taken along a line A-A of FIG. 1(a) and a line B-B of FIG. 1(b), respectively. FIG. 4 is an exploded perspective view of an irradiation unit 4. FIG. 5(a) is a front view illustrating the irradiation unit 4, and FIG. 5(b) is a cross-sectional view taken along a line C-C of FIG. 5(a). FIG. 6(a) is a front view illustrating the light orientation controller 6 and body cover 3, and FIG. 6(b) is a cross-sectional view taken along a line D-D of FIG. 6(a). FIG. 7 is a perspective view of the irradiation unit 4. FIG. 8 is a block diagram of a control circuit provided within a body 2 and the light orientation controller 6.

The light irradiation device 1 according to the embodiment of the present invention irradiates a biological body surface, especially, a skin surface, with light to perform optical hair removal removing hair in the biological body surface, optical hair reduction inhibiting reproduction and growth of hair in the biological body surface, or the like.

The light irradiation device 1 according to the embodiment of the present invention includes the body 2 which can be gripped by one hand, the irradiation unit 4 as a light irradiation means, the light orientation controller 6, and the body cover 3. The irradiation unit 4 is detachably attached to an irradiation side end 2c at one end of the body 2, and includes a lens 5 at the top and a light source 9 inside. The light orientation controller 6 covers the irradiation unit 4, and controls light projected from the irradiation unit 4. The body cover 3 holds the light orientation controller 6, and is detachable from the body 2.

The body 2 includes an internal battery 2x and a controller 2y controlling light irradiation. The body 2 further includes an attachment operation portion 2a and a power switch 2b on an exterior. The attachment operation portion 2a is used to operate attachment and detachment of the body cover 3. The power switch 2b turns on and off a power source of the body 2. At the irradiation-side end 2c of the body 2, to which the irradiation unit 4 is attached, a pair of substantially U-shaped unit attachments 2d, a body-side connector 33, a body-side engagement portion 34, and a not-shown light emission switch are provided. The unit attachments 2d allow the irradiation unit 4 to be attached and detached. The body-side connector 33 protrudes from the irradiation-side end 2c, and electrically connects the body 2 and irradiation unit 4. The body-side engagement portion 34 is operated by the attachment operation portion 2a to detachably engage the body cover 3. The light emission switch causes the light source 9 of the irradiation unit 4 to emit light.

The body cover 3 includes a cover member 31, a cover-side engagement portion 32, and the light orientation controller 6 which is a cylindrical float block. The cover-side engagement portion 32 allows the cover member 31 to be detachably engaged with the body-side engagement portion 34. The light orientation controller 6 includes an emission portion 6a emitting light of the irradiation unit 4 to the outside. The cover member 31 includes an opening for the light orientation controller 6 covering the irradiation-side end 2c and irradiation unit 4. The light orientation controller 6 is slidably held by the opening. The body cover 3 includes a fixing means 3a fixing the light orientation controller 6. The light orientation controller 6 is made of a light shielding member. The irradiation unit 4 is located in space within the light orientation controller 6. Provision of the irradiation unit 4 within the light orientation controller 6 prevents light of the irradiation unit 4 from leaking out through other than the emission portion 6a of the light orientation controller 6.

The irradiation unit 4 is attached to the cover member 31 so as to float in a light irradiation direction F that light is projected, to be specific, in the direction orthogonal to the emission portion 6a of the light orientation controller 6. The irradiation unit 4 includes a lamp casing 8 and the light source 9 inside the same. The lamp casing 8 is composed of two front and rear parts and includes a substantially rectangular irradiation port 42 at one end. In the irradiation port 42, the lens 5 is fit as a lid. On both longitudinally outer sides of the irradiation unit 4, to be specific, at both longitudinal ends of the lens 5, attachment protrusions 4a are extended so as to be freely engaged with the unit attachment portions 2d. The attachment protrusions 4a are engaged with the unit attachment portions 2d to allow the irradiation unit 4 to be detachably attached to the body 2.

The bottom part of the irradiation unit 4 at an end portion opposite to the irradiation port 42 includes a recess 45 at the substantially center. The recess 45 is connected to an irradiation-side connector 12 which is electrically connected to the body-side connector 33 when the body 2 is attached. The recess 45 of the irradiation unit 4 is aligned with the position where the body-side connector 33 protrudes at the irradiation-side end 2c by holding the both outer sides in a short-side direction which are substantially orthogonal to the both outer sides with the attachment protrusions 4a of the lamp casing 8 extended. In such a manner, the irradiation unit 4 and body 2 are positioned at the attachment positions. The irradiation unit 4 is then pressed in a direction opposite to the light irradiation direction F to press each of the attachment protrusions 4a into between the clicks of the corresponding U-shaped unit attachment portion 2d. Each of the attachment protrusions 4a is sandwiched between the clicks of the unit attachment portion 2d, thus attaching the irradiation unit 4 to the body 2.

To detach the irradiation unit 4 from the body 2, the both outer sides of the lamp casing 8 in the short-side direction is grasped in a state where the irradiation unit 4 is attached to the body 2, and the irradiation unit 4 is pulled in the light irradiation direction F. The attachment protrusions 4a get out from between the clicks of the unit attachment portions 2d, allowing the irradiation unit 4 to be detached from the body 2.

In the both outer sides of the lamp casing 8 in the short-side direction, a plurality of slits 8b as openings connecting the inside and the outside of the irradiation unit 4 are provided so as to extend in the longitudinal direction. By providing the slits 8b, heat within the irradiation unit 4 is released to the outside through the slits 8b, thus preventing an increase in temperature within the irradiation unit 4.

The irradiation unit 4 includes a reflector 10, a base 16, and a circuit unit 11 within the lamp casing 8 covered with the lens 5. The reflector 10 reflects light from, for example, a xenon tube as the tubular light source 9 elongated in the longitudinal direction of the lamp casing 8 so that the light is directed to the lens 5 fit into the irradiation port 42. The base 16 holds the reflector 10 together with the lens 5 with an elastic member 14 interposed therebetween. The circuit unit 11 is composed of a trigger transformer and is configured to receive an electric signal transmitted from the irradiation-side connector 12 and apply trigger voltage to the light source 9, causing the light source 9 to emit light. The circuit unit 11 includes a circuit printed board 13 with the connector 12 mounted thereon. The reflector 10 has a substantially U-like cup shape which includes a reflection surface inside and an opening of substantially same size as that of the irradiation port 42 on the irradiation port 42 side. The light source 9 is located inside bottom part of the cup shape on the opposite side of the opening of the reflector 10. The reflector 10 and lens 5 equalize light from the light source 9. To be specific, the reflector 10 aligns the direction of light generated by light emission of the light source 9 with the direction orthogonal to the irradiation port 42 and substantially equalizes the distribution of the intensity of light projected from the irradiation port 42. In the longitudinal direction of the bottom part of the cup shape located at the opposite side of the opening, insertion holes 10a allowing the light source 9 to be inserted therethrough are provided. By inserting the light source 9 through the insertion holes 10a, the light source 9 is located within the reflector 10. The light source 9 of the irradiation unit 4 is not limited to a xenon tube and may be composed of one or a plurality of diodes. At both ends of the light source 9, which is inserted through the insertion holes 10a, in the longitudinal direction as an axial direction, substantially doughnut-shaped elastic rubber plates, for example, are fit as fixtures 15. Two of the fixtures 15 face each other and are brought into contact with the respective side surfaces of the reflector 10 where the insertion holes 10a are formed. The fixtures 15 sandwich the reflector 10 on the both sides and elastically fix the light source 9 to the reflector 10.

The base 16 includes a seating portion 16a holding the bottom of the reflector 10, and a side portion 16b protruding from the seating portion 16a and holding the rear side of the reflection surface. The base 16 includes a plurality of openings through which heat due to light emission of the light source 9 is released from the light source 9 and reflector 10.

Between the bottom of the reflector 10 and the base 16, for example, a substantially plate-shaped rubber plate is provided as the elastic member 14. One surface of the elastic member 14 abuts on the bottom of the reflector 10, and the other surface of the elastic member 14 abuts on the base 16.

The side portion 16b of the base 16 is provided with the holding engagement portion 16c engaged with a part of the outer circumference of the lens 5, and the base 16 and an engaged portion 5a of the lens 5 are engaged by the holding engagement portion 16c. The four sides forming the opening of the reflector 10 abut on the lens 5. The elastic member 14 is sandwiched and compressed between the base 16 and lens 5, so that the lens 5 and base 16 elastically hold the reflector 10. The fixtures 15 may be formed integrally with the elastic member 14.

At the end of the reflector 10 abutting on the lens 5, a plurality of protrusions are extended so as not to close the openings of the reflector 10. The protrusions are not illustrated in the embodiment. When the reflector 10 is elastically held, the end of the reflector 10 is not in direct contact with the lens 5, but the protrusions are in point contact with the lens 5. Since the reflector 10 and lens 5 are in point contact, heat due to light emission is prevented from being transmitted to the lens 5 through the reflector 10. The protrusions are provided for six places, for example: four corners at which the sides of the reflector 10 are connected; and middle points of the two sides elongated in the longitudinal direction. The protrusions have a diameter substantially the same as the thickness of the reflector 10, to be specific, the thickness from the reflection surface to the rear surface and are extended in the light irradiation direction F.

The irradiation unit 4 including the light source 9 can be detached from the body 2 and can be engaged and disengaged by a method not requiring an attachment tool such as a screwdriver for attachment and detachment. Accordingly, tools are not necessary to attach or detach the irradiation unit 4 from the body 2, and the light source 9 can be easily detached when the light source 9 deteriorates or fails. Moreover, since the light source 9 which deteriorates with time or fails can be easily replaced, it is possible to project a stable intensity of light in long period. The term "long period" in the present invention means years when the light irradiation device 1 of the present invention is used several times each day to repeatedly perform light irradiation and does not mean time when the light irradiation device 1 is used once to perform light irradiation continuously several times. In such a manner, the light source 9, reflector 10, and lens 5, which are susceptible to heat due to light emission, are integrated as the irradiation unit 4. Accordingly, even when the light source 9, reflector 10, and lens 5 are deteriorated or deformed due to long-period use of the light irradiation device 1 to cause misalignment of the light source 9, the misalignment of the light source 9 can be easily corrected by replacing the irradiation unit 4. It is therefore possible to project a stable intensity of light in longer period.

Furthermore, by elastically fixing the light source 9 to the reflector 10 using the fixtures 15 and elastically holding the reflector 10 between the lens 5 and base 16 with the elastic member 14 interposed therebetween, the light source 9 is prevented from being shifted with respect to the lens 5 and the reflector 10. Moreover, the fixtures 15 and elastic member 14 reduce and absorb vibration and shock caused when the emission portion 6a of the light orientation controller 6 is pressed against the biological surface for light irradiation or when the irradiation unit 4 is attached or detached from the body 2. It is therefore possible to inhibit the shift of the light source 9 and reflector 10 within the irradiation unit 4 to prevent the misalignment of the light source 9, to be specific, prevent light projected from the irradiation port 42 from being not uniform, projecting a stable intensity of light in the long period.

The light orientation controller 6 is located between the irradiation unit 4 and the skin surface. As illustrated in FIG. 7, the light orientation controller 6 includes: a cylindrical light shielding portion 6b made of an opaque material not transmitting light; and an emission portion 6a provided at a substantially rectangular open end of the cylindrical light shielding portion 6b. The emission portion 6a is provided with a lens as an optics, for example. The light shielding portion 6b is formed into a cylindrical shape which covers the side surface of the irradiation unit 4, and the surface thereof covering the irradiation unit 4 is extended in the light irradiation direction that the irradiation unit 4 projects light from the irradiation port 42 onto the skin surface. The light orientation controller 6 is located facing the opening of the cylinder and the irradiation port 42 of the irradiation unit 4. The opening located at the extended part of the light orientation controller 6 serves as an emission port through which light from the irradiation unit 4 is emitted to the outside, and the end of the light shielding portion 6b constituting the emission port is brought into contact with the skin surface at light irradiation. The light irradiation direction refers to as a direction orthogonal to the opening face of the irradiation unit 42. The intensity of light is equalized by the reflector 10 and lens 5, and the light is projected through the emission portion 6a. The emission portion 6a is formed so as to equalize the intensity of light without changing the intensity or direction of the light incident from the irradiation unit 4. For example, in the embodiment of the present invention, the emission portion 6a is partitioned by the plurality of partition members 6a1 into a plurality of compartments 6a2 arranged side by side.

The light irradiation onto the biological surface is performed though the emission portion 6a by causing the irradiation unit 4 to emit light with the light orientation controller 6 pressed against the biological surface. The partition members 6a1 prevent that the skin protrudes into internal space of the light shielding portion 6b and comes into contact with the irradiation unit 4, especially, the lens 5 when the orientation controller 6 is pressed against the biological surface. Moreover, the partition members 6a1 are made of a light permeable member so as to equalize the intensity of light projected from the irradiation unit 4.

The light shielding portion 6b is provided with hooks 6b1 at both right and left sides, and the hooks 6b1 are fit to the body cover 3 to hold the light orientation controller 6. In side surfaces of the light shielding portion 6b including edges forming the longitudinal direction of the opening, slide guides 6b2 and 6b4 are provided along the light irradiation direction orthogonal to the opening. The slide guides 6b2 and 6b4 allow the light orientation controller 6 to slide in parallel to the light irradiation direction when the light irradiation device 1 is assembled. In one of the side surfaces of the light shielding portion 6b, a switch protrusion 6b3 is protruded in parallel to the side surface substantially at the center of the edge forming the opening opposite to the emission port. The switch protrusion 6b3 activates a light emission switch when the light orientation controller 6 slides by the slide guides 6b2 and 6b4. When the part forming the emission port is brought into contact with the biological surface and then pressed in the light irradiation direction or against the skin surface while the power switch 2b is on, the light orientation controller 6 slides in the direction opposite to the light irradiation direction. When the light orientation controller 6 slides, the switch protrusion 6b3 presses the light emission switch, and the pressed light emission switch causes the light source 9 through a unit circuit to emit light. After light irradiation, the light orientation controller 6 is slid in the light irradiation direction to separate the switch protrusion 6b3 from the light emission switch, thus releasing the pressed light emission switch. This light irradiation operation is just an example. Certainly, light irradiation may be performed by turning on the power switch 2b in a state where the part forming the emission port is pressed against the biological surface and the light emission switch is turned on. Alternatively, the light irradiation device 1 may be provided with another type of irradiation switch.

As illustrated in FIG. 8, the light orientation controller 6 is controlled by a control circuit provided with the body 2 and orientation controller 6. The control circuit includes: a microprocessor unit (MPU) 21; a charge controller 22 having an Li ion cell with an adaptor and a protective IC; a capacitor charger 23 having a strobe capacitor and a voltage control IC for the same; a flash controller 24 controlling a trigger for the light source 9; and a peripheral circuit 25. Controls of light irradiation performed by the control circuit include, for example, control of the number of times that light is successively irradiated or the total intensity of light of the irradiation unit 4, safety management including detection of temperature of the irradiation unit 4 or detection of the presence of the body cover 3 or irradiation unit 4, and the like. The designs thereof can be properly changed.

Figure 9:
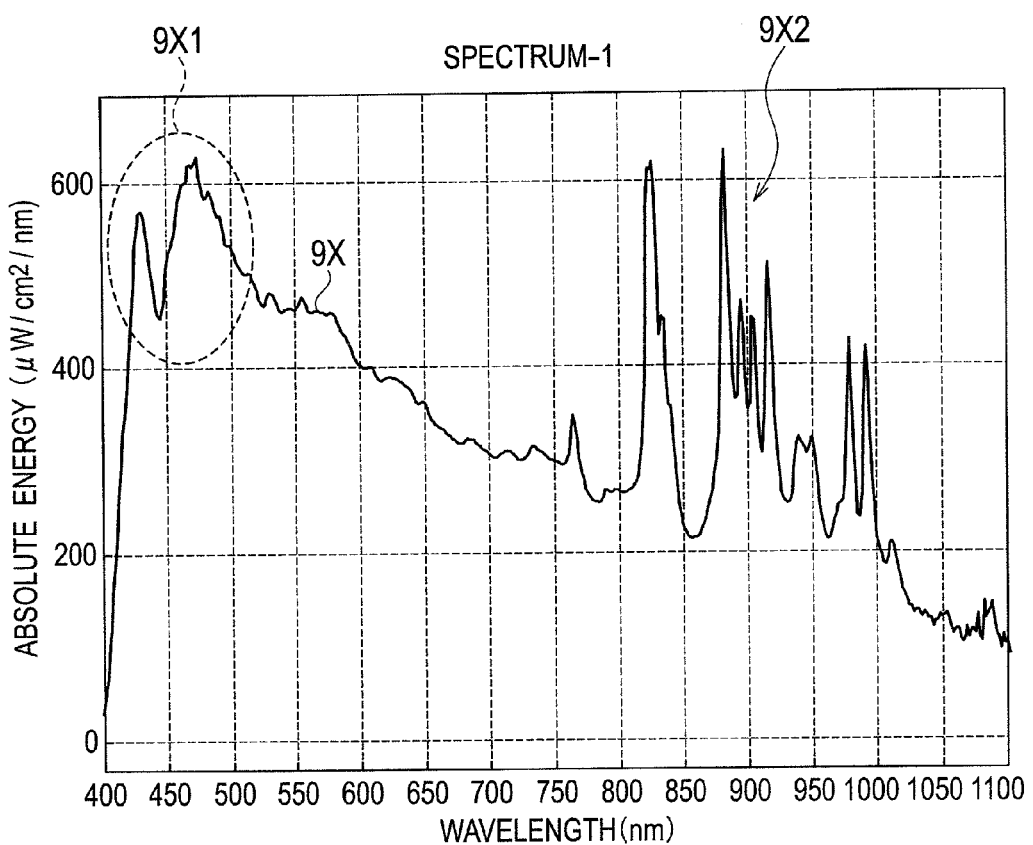
FIG. 9 is a diagram illustrating a wavelength distribution of irradiated light.
Figure 10:
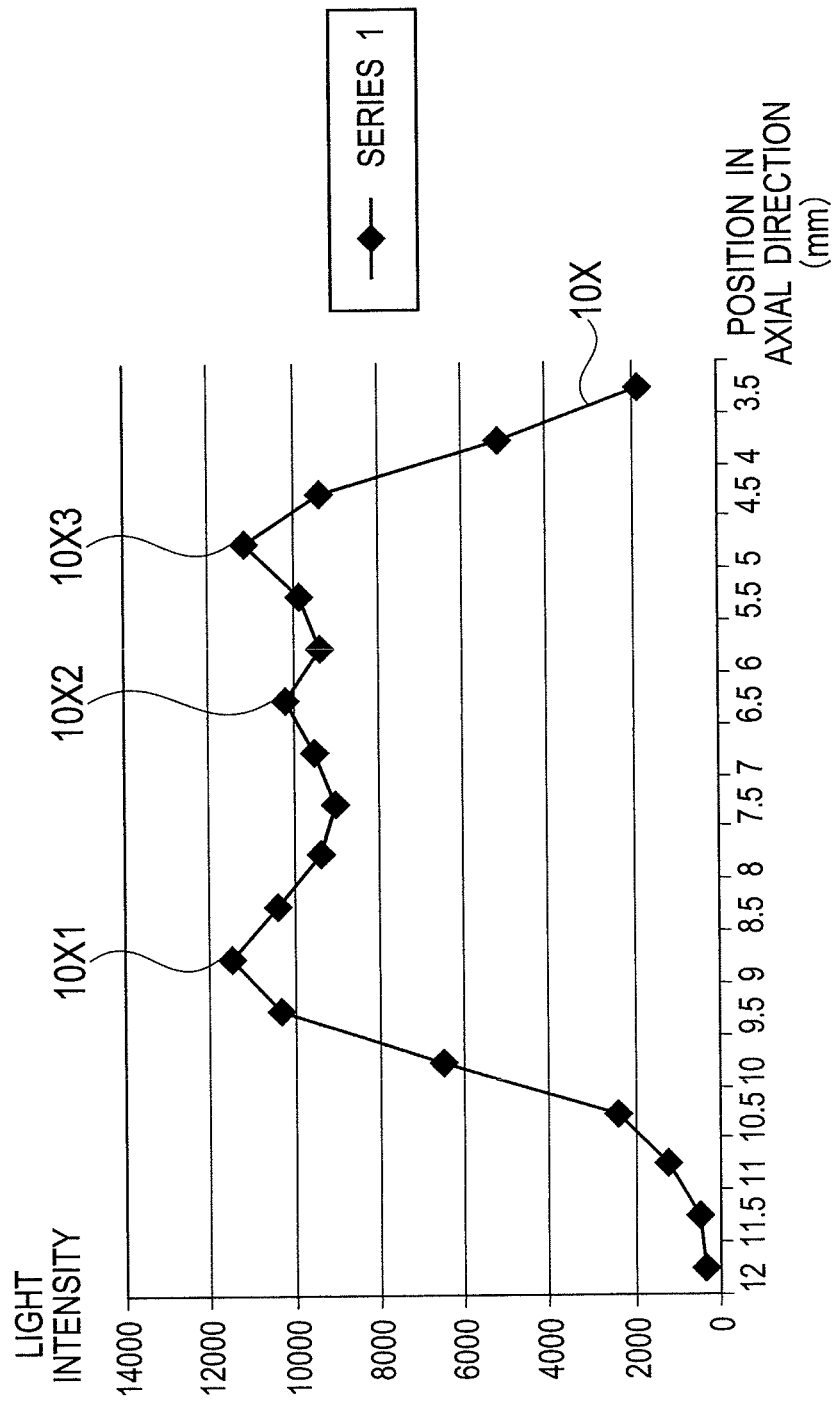
FIG. 10 is a diagram illustrating a light intensity distribution at a lens in a lens width direction.

For example, when the light source 9 is a xenon flash lamp, a voltage of 300 V is applied across both ends of the xenon tube. The voltage is then increased by the trigger transformer to apply 5 kV to the surface of the xenon tube. Gas within the xenon tube is therefore ionized, and passage of current (110 A, 1 ms) causes the xenon tube to emit light. FIG. 9 illustrates a wavelength distribution (spectrum distribution) 9x of light emitted and projected to the skin surface under this condition. As illustrated in FIG. 9, the spectrum distribution 9x includes a first high energy part 9X1 in a wavelength range of 400 to 500 nm and a second high energy part 9X2 in a wavelength range of 800 to 1000 nm. The light projected from the lens 5 is optically designed so as to have a light intensity distribution 10X illustrated in FIG. 10 at the position of 5 mm from the front surface of the lens 5 as an outgoing surface through the light orientation controller. The light intensity distribution 10x illustrates a distribution of light intensity of the lens 5 in a lens width direction (in a direction indicated by an arrow 5X) and has local maximum values 10X1, 10X2, and 10X3.

The light orientation controller 6 prevents the light source 9 from coming into direct contact with the skin surface. Moreover, the light shielding portion 6b covering the light source 9 prevents irradiated light from leaking out, and the partitioning members 6a1 of the emission portion 6a where the optics is provided prevents the skin surface from protruding into the light irradiation device 1, thus preventing the possibility that the skin surface can come into contact with the light source 9 as the light irradiation means and suffer from burns or the like. Furthermore, the intensity of light projected from the emission portion 6a is equalized for irradiation. Accordingly, the skin surface can be irradiated with a stable intensity of light.

In the light irradiation device 1 according to the embodiment of the present invention, with the aforementioned configuration, light in a wavelength range in 400 to 1200 nm is distributed as pulses having a full width at half maximum of 600 to 1200 μs so as to have energy intensity of 0.2 to 10 J/cm$^2$ at a distance of 5 mm from the front surface of the lens 5. For this light has low power, even if the light is projected onto the skin surface, the light will not cause burns, spots, or the like in the skin, thus giving little burden to the skin.

Figure 11:
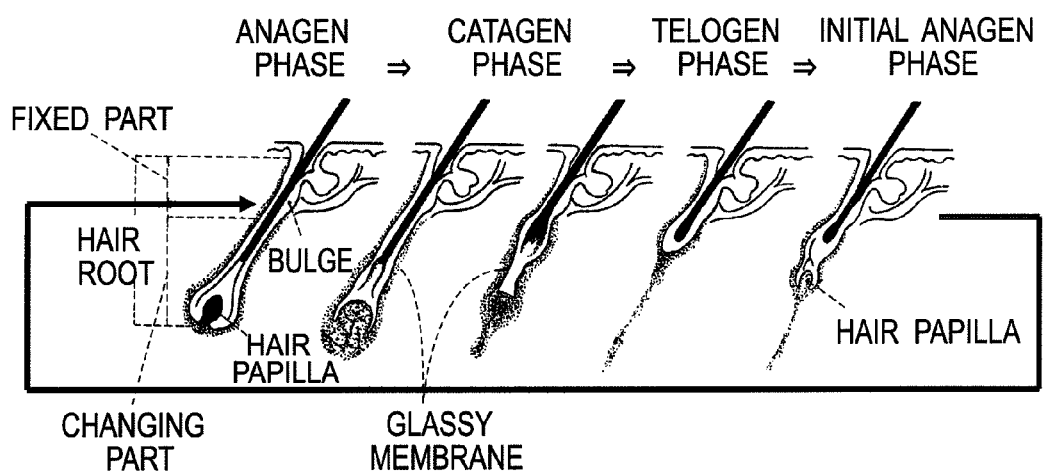
FIG. 11 is an explanatory view illustrating a hair cycle.

The pulses of light given through the outgoing surface of the light irradiation device 1 are applied to skin with body hair removed by waxing, for example. FIG. 11 illustrates a hair cycle. The hair cycle is reset by hair removal. Herein, if hair in the anagen phase is irradiated with light by the light irradiation device 1 according to the embodiment of the present invention, for example, expression of I11b in the skin surface increases, and expression of shh and/or Bmp decreases. This will inhibit proliferation and/or differentiation of follicle cells, thus inhibiting the growth of hair. Moreover, if temporary stress is given to cells to promote expression or activation of stress-responsive genes, expression or activation of MAP kinase p38, JNK (c-Jun N-terminal kinase), and the like, for example, is promoted, making it possible to stop, inhibit, or change the cell cycle of follicle cells. For example, light irradiation can generate reactive oxygen species, radicals, and the like which then act as cellular stress. This promotes expression or activation of the aforementioned genes to stop, inhibit, or change the cell cycle of follicle cells. The surrounding cells will therefore stop growing or go through apoptosis to die. In such a manner, the growth of hair is inhibited by directly or indirectly inducing apoptosis.

As described above, by using the light irradiation device 1 according to the embodiment of the present invention to irradiate skin with hair removed, it is possible to easily obtain hair removal or reduction effect at home with irradiation of lower power light without giving burden to the skin and eliminate the need for operations by expert doctors.

The circuit design is changed so that the capacitance of a main capacitor which is incorporated in the capacitor charger 23 and stores electric energy used for light emission of the irradiation unit is doubled, for example, from 400 to 800 μF. The capacitance of the main capacitor affects the intensity of emitted light. Doubling the capacitance of the main capacitor increases the intensity of emitted light.

Furthermore, a not-shown filter cutting off short wavelength components is provided between the front surface of the lens 5 and the light orientation controller 6 to reduce low frequency components. By cutting off the short wavelength components and increasing power of the long wavelength components, the light source 9 serves as a long-wavelength high-power light source. The light source 9 therefore penetratingly acts deep into the skin and causes melanin to absorb light to increase the hair removal and reduction effect. Moreover, by cutting the absorption peak of blood, it is possible to reduce the occurrence of inflammation due to light absorption of blood (blood vessels), which is a side effect, thus reducing the burden on the skin.

In such a manner, the change of the circuit design and the provision of the filter enable light irradiation with less burden on the skin. The hair removal and reduction effect can be obtained by distributing 550 to 1200 nm wavelength light as pulses having a full width at half maximum of 600 to 1200 μs so that the light has energy intensity of 0.2 to 10 J/cm$^2$ at a distance of 5 mm from the front surface of the lens 5.

The absorption wavelength of pigment contained in the skin (melanin) depends on the race of a person to be irradiated with light. Accordingly, the wavelength and irradiation energy of the light source to be used is appropriately set according to the spectral absorptance of melanin. If the skin contains a lot of eumelanin, the irradiation energy is increased in a long-wavelength range with high penetration depth so as to increase the absorption deep in the skin. On the other hand, if the skin contains a lot of pheomelanin, the spectral absorptance is low in the long-wavelength range. Accordingly, the irradiation light is configured so as to include shorter wavelength components than that in the case where the skin contains a lot of eumelanin, and at least the absorption peak of blood vessels is cut off, thus increasing the absorption efficiency deep in the skin. Moreover, by using the light source according to the spectral absorptance of melanin contained in the skin, it is possible to provide a light irradiation device capable of easily removing and reducing hair with less side effect without giving burden to the skin.

EXAMPLES

Hereinafter, a description is given of the light irradiation device according to the embodiment of the present invention more specifically using examples. However, the scope of the invention is not limited by these examples.

In order to confirm the hair removal and reduction effect of the light irradiation device according to the embodiment of the present invention, evaluation tests described below were carried out.

Example 1

The back skins of C57BL/6 mice with follicles being in the telogen phase not in the anagen phase were subjected to waxing hair removal to induce the anagen phase of hair. Irradiation was started five days after the hair removal. The irradiation condition was that 400 to 1200 nm wavelength light was distributed as pulses of a full width at half maximum of 600 μs so as to have energy intensity of 0.2 to 0.25 J/cm$^2$ at a distance of 5 mm from the front surface of the lens 5. The capacity of the main capacitor was set to 400 μF at this time. The irradiation was continuously performed for an area of 1×3 cm five times a day. The irradiated mice were observed over time, or the skins thereof were sampled. The skin sampling was performed within 2 hours, 12 hours, one day, three days, and seven days after the irradiation. At the sampling, in order to cause BrdU to enter growing cells, BrdU (100 μg/g bodyweight) was injected into abdominal cavities one hour before the sampling.

<Method of Producing Tissue Sections>

1. Cervical dislocation was performed for each mouse for skin sampling.

2. 70% ethanol was poured over the back skins of the mice, and the back skin was wiped with tissue paper or KimWipes to remove sebum on the skin surface.

3. The skin was cut according to the irradiation area. In this experiment, the irradiation area was set to 1×3 cm, and accordingly, an area of about 0.7×2 cm considered to be surely irradiated was cut out. The control group not irradiated was cut in a similar manner.

4. The cut out skin was immersed in 1×PBS(-).

5. The skin was further cut into a necessary size of 0.2×0.5 cm with a scalpel.

6. The skin was sandwiched by meshes to be fixed flat according to the necessity.

7. The skin was fixed in phosphate buffer neutral formalin for three hours or in rapid tissue fixative (KURABO) for one hour.

8. The skin was washed with 1×PBS(-) for 10 minutes for 3 times.

9. The skin was immersed in 70% ethanol. The skin is conservable at 4° C. several days. When the experiment was immediately advanced to the next step, the skin was left shaking slowly at room temperature for 30 minutes.

10. Thereafter, liquid exchange was performed as follows, and then the skin was embedded in paraffin.
   99.5% ethanol, 30 min×2 times
   100% ethanol, 30 min×2 times
   xylene, 30 min×3 times
   xylene/paraffin (45° C.), 30 min×1 time
   paraffin (60° C.), 30 min×3 times 11. The embedded block was cut into sections of 4 to 5 μm by a sliding microtome.

<Method for Immunostaining>

A glass slide with each tissue section attached thereto was immersed in liquids in the following procedure to be deparaffinized.
   xylene, 10 min×3 times
   99.5% ethanol, 5 min×4 times
   1×PBS(−), about 5 min The sample was surrounded using a DAKO pen (DAKO) so as not to dry.
   1×PBS(−) was put on the sample.
The subsequent process depended on the antibody.

<BrdU Staining>
1. 2N HCl was put on the sample and was incubated at room temperature for 20 minutes.
2. The sample was washed with 1×PBS(−).
3. 0.1% trypsin was put on the sample and incubated at 37° C. for 5 minutes.
4. The sample was washed with 1×PBS(−).
5. 1% BSA was put on the sample and was blocked at room temperature for 30 minutes.
6. Anti-BrdU antibody (DAKO corporation) was diluted by 1/200 and put on the sample.
7. The sample was reacted at 4° C. for one night or at room temperature for two hours.
8. The sample was washed with 1×PBS(−) for 5 minutes for 3 times.
9. A secondary antibody was reacted. This was conducted at room temperature for 30 minutes using donkey anti-mouse IgG Alexa Flour 594 (1/2000-3000, Invitrogen).
10. The sample was washed with 1×PBS(−) for 5 minutes for 3 times.
11. A droplet of 1000-fold diluted DAPI (0.5 mg/ml) was dropped on the sample, and the sample was enclosed.

<ssDNA Staining>
1. 0.4 to 0.8 mg/ml proK was put on the sample and reacted at room temperature for 15 minutes.
2. The sample was washed with 1×PBS(−).
3. 1% BSA was put on the sample and blocked at room temperature for 30 minutes.
4. Anti-ssDNA antibody (DAKO corporation) was diluted by 1/100 and was put on the sample.
5. The sample was reacted at 4° C. for one night or at room temperature for two hours.
6. The sample was washed with 1×PBS(−) for 5 minutes for 3 times.
7. A secondary antibody was reacted. This was conducted at room temperature for 30 min using donkey anti-mouse IgG Alexa Flour 488 (1/1000-2000, Invitrogen).
8. The sample was washed with 1×PBS(−) for 5 minutes for 3 times.
9. A droplet of 1000-fold diluted DAPI (0.5 mg/ml) was dropped on the sample, and the sample was enclosed.

<Microscopic Observation>

The used microscope was OLIMPUS BX-50. The object lens had a magnification of 10, and the filters were WU (DAPI staining), WIY (Alexa594), and NIBA (Alexa488). The digital camera was Pixera penguin 150CLM.

<RNA Extraction—Real Time Method>
1. Pieces of skin of about 1.5×0.5 cm were cut out, sandwiched by aluminum foils, and then put into liquid nitrogen.
2. Each piece to be reserved was put into a deep freezer at −80° C.
3. Each piece of the skin was crushed by a Cryo-press (Microtech nition). The cells were crushed after being sufficiently cooled with liquid nitrogen.
4. Using the crushed skin, RNA extraction was performed by the RNeasy Fibrous Tissue Mini Kit (QIAGEN).
5. Using RNA of 1 cDNA is synthesized by the Quantitect Reverse Transcription Kit (QIAGEN).
6. Realtime PCR was performed using SYBR Premix Ex Taq II (Takara) as a SYBR reagent and Thermal Cycler Dice (Takara) as a device. The primers were following sets made of Takara.

<Primer>

MA082472-F, MA082472-R (Egfr); MA080988-F, MA080988-R (Hgf); MA029052-F, MA029052-R (Ikbkb); MA025939-F, MA025939-R (Il1b); MA081429-F, MA081429-R (Mitf); MA073973-F, MA0739373-R (Nfkb1); MA057895-F, MA057895-R (Nfkb2); MA076991-F, MA076991-R (Shh); MA079248-F, MA079248-R (Stat3); MA030397-F, MA030397-R (Tgfb1); MA027420-F, MA027420-R (Tgfb2); MA078455-F, MA078455-R (Map3k5); MA032002-F, MA032002-R (Mapk8); MA050368-F, and MA050368-R (Actb)

<Observation Result>

Figure 12:
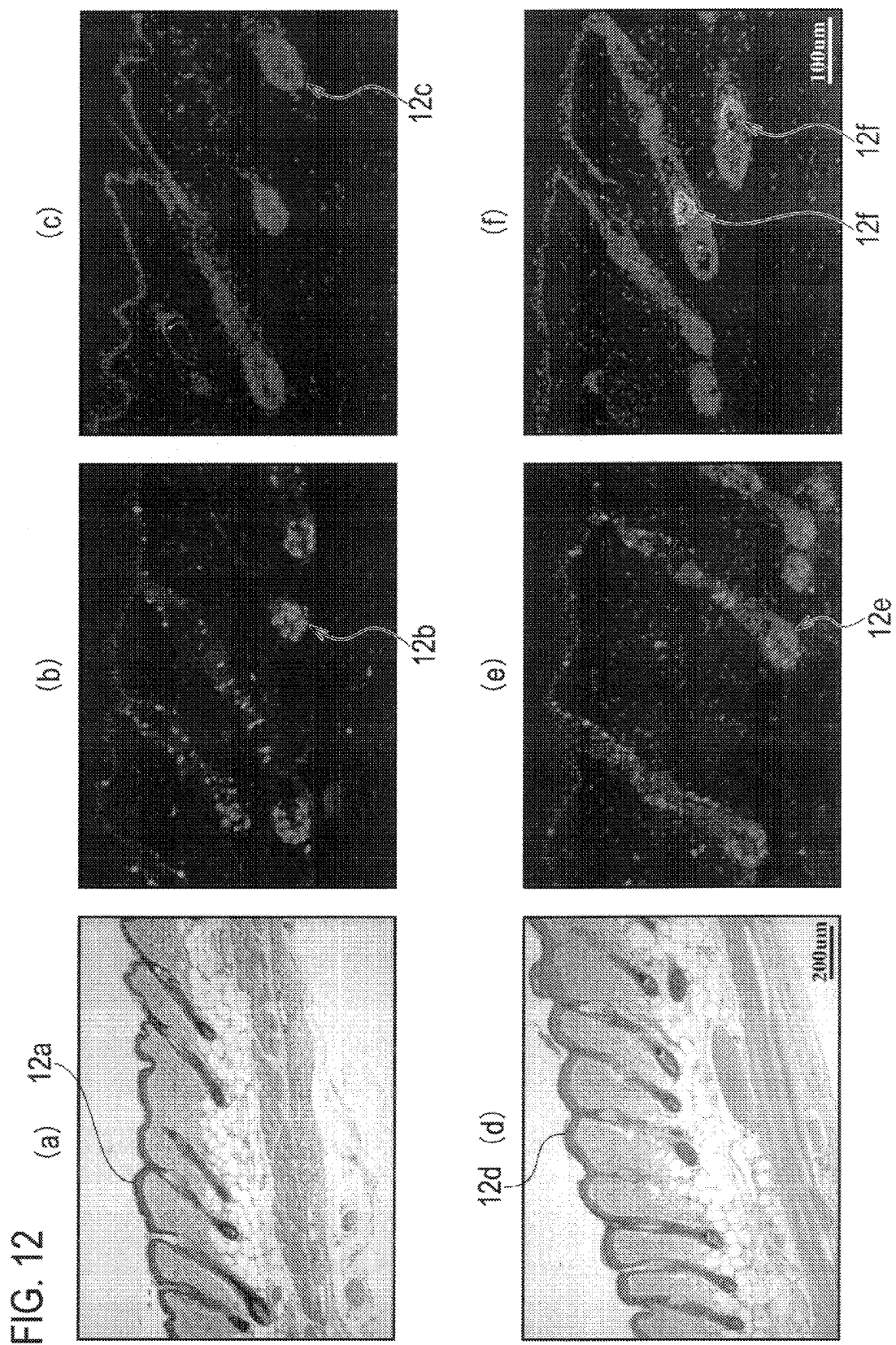
FIG. 12(a) is a micrograph illustrating a result of HE staining of control mouse skin.
FIG. 12(b) is a micrograph illustrating a result for control mouse skin in the case of using an anti-BrdU antibody.
FIG. 12(c) is a micrograph illustrating a result for control mouse skin in the case of using an anti-ssDNA antibody.
FIG. 12(d) is a micrograph illustrating a result of HE staining of control mouse skin 10 hours after irradiation.
FIG. 12(e) is a micrograph illustrating a result for control mouse skin 10 hours after irradiation in the case of using an anti-BrdU antibody.
FIG. 12(f) is a micrograph illustrating a result for control mouse skin 10 hours after irradiation in the case of using an anti-ssDNA antibody.

FIGS. 12(a) to 12(f) illustrate microscopic observation results at 10 magnifications 10 hours after irradiation. FIGS. 12(a) to 12(c) illustrate observations of mouse skins of the control group not irradiated with light. FIG. 12(a) illustrates a result of HE staining, FIG. 12(b) illustrates a result in the case of using an anti-BrdU antibody, and FIG. 12(c) illustrates a result in the case of using an anti-ssDNA antibody. FIGS. 12(d) to 12(e) illustrate observations of mouse skins irradiated with light. FIG. 12(d) illustrates a result of HE staining, FIG. 12(e) illustrates a result in the case of using an anti-BrdU antibody, and FIG. 12(f) illustrates a result in the case of using an anti-ssDNA antibody. Based on the results of HE staining illustrated in FIGS. 12(a) and 12(d), there were no observable changes in the skin surfaces as indicated by 12a and 12d. As indicated by 12b and 12e in FIGS. 12(b) and 12(e), there were very few differences in the distribution region and the number of BrdU positive cells. As indicated by 12c and 12f in FIGS. 12(c) and 12(f), there was ssDNA positive portion (12f) in the group irradiated with light, which shows the possibility that cellular death (apoptosis) was occurred.

Figure 13:
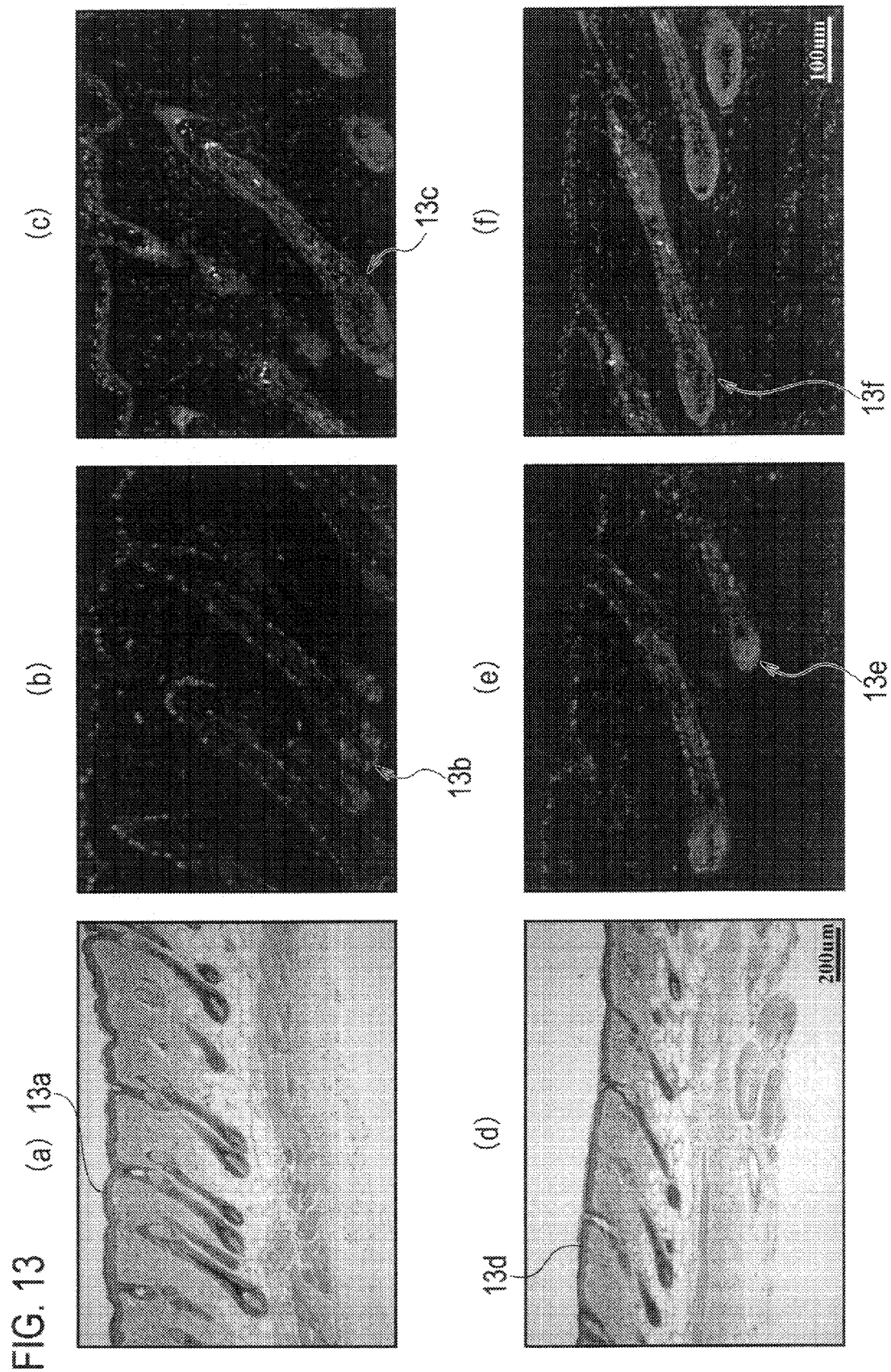
FIG. 13(a) is a micrograph illustrating a result of HE staining of control mouse skin.
FIG. 13(b) is a micrograph illustrating a result for control mouse skin in the case of using an anti-BrdU antibody.
FIG. 13(c) is a micrograph illustrating a result for control mouse skin in the case of using an anti-ssDNA antibody.
FIG. 13(d) is a micrograph illustrating a result of HE staining of control mouse skin 24 hours after irradiation.
FIG. 13(e) is a micrograph illustrating a result for control mouse skin 24 hours after irradiation in the case of using an anti-BrdU antibody.
FIG. 13(f) is a micrograph illustrating a result for control mouse skin 24 hours after irradiation in the case of using an anti-ssDNA antibody.

FIGS. 13(a) to 13(f) illustrate microscopic observation results at 10 magnifications 24 hours (1 day) after irradiation. FIGS. 13(a) to 13(c) illustrate observations of mouse skin of the control group not irradiated with light. FIG. 13(a) illustrates a result of HE staining, FIG. 13(b) illustrates a result in the case of using anti-BrdU antibody, and FIG. 13(c) illustrates a result in the case of using anti-ssDNA antibody. FIGS. 13(d) to 13(e) illustrate observations of mouse skin irradiated with light. FIG. 13(d) illustrates a result of HE staining, FIG. 13(e) illustrates result in the case of using an anti-BrdU antibody, and FIG. 13(f) illustrates a result in the case of using an anti-ssDNA antibody. As indicated by 13b in FIG. 13(a), the epidermis of the control group was a little thickened. As indicated by 13b in FIG. 13(b), many BrdU positive cells were observed in the control group. This can be thought to be because the control mice might scratch their skin or been injured. As illustrated in FIG. 13(f), it is observed in follicles of the irradiated group that melanocytes including melanin which had undergone cellular death within 10 hours or some of keratinocytes were extruded upward from hair matrix cells.

Figure 14:
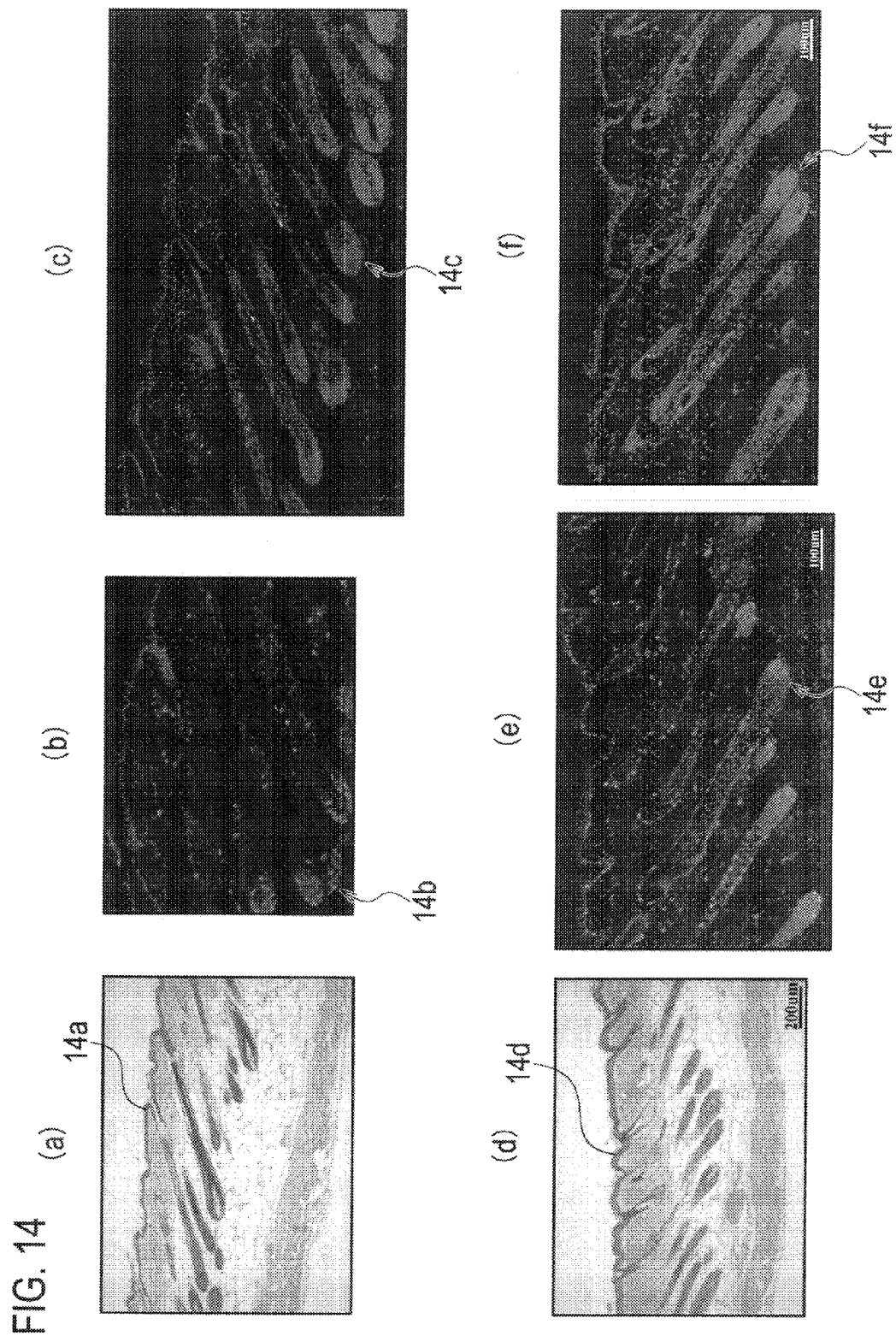
FIG. 14(a) is a micrograph illustrating a result of HE staining of control mouse skin.
FIG. 14(b) is a micrograph illustrating a result for control mouse skin in the case of using an anti-BrdU antibody.
FIG. 14(c) is a micrograph illustrating a result for control mouse skin in the case of using an anti-ssDNA antibody.
FIG. 14(d) is a micrograph illustrating a result of HE staining of control mouse skin three days after irradiation.
FIG. 14(e) is a micrograph illustrating a result for control mouse skin three days after irradiation in the case of using an anti-BrdU antibody.
FIG. 14(f) is a micrograph illustrating a result for control mouse skin three days after irradiation in the case of using an anti-ssDNA antibody.
Figure 15:
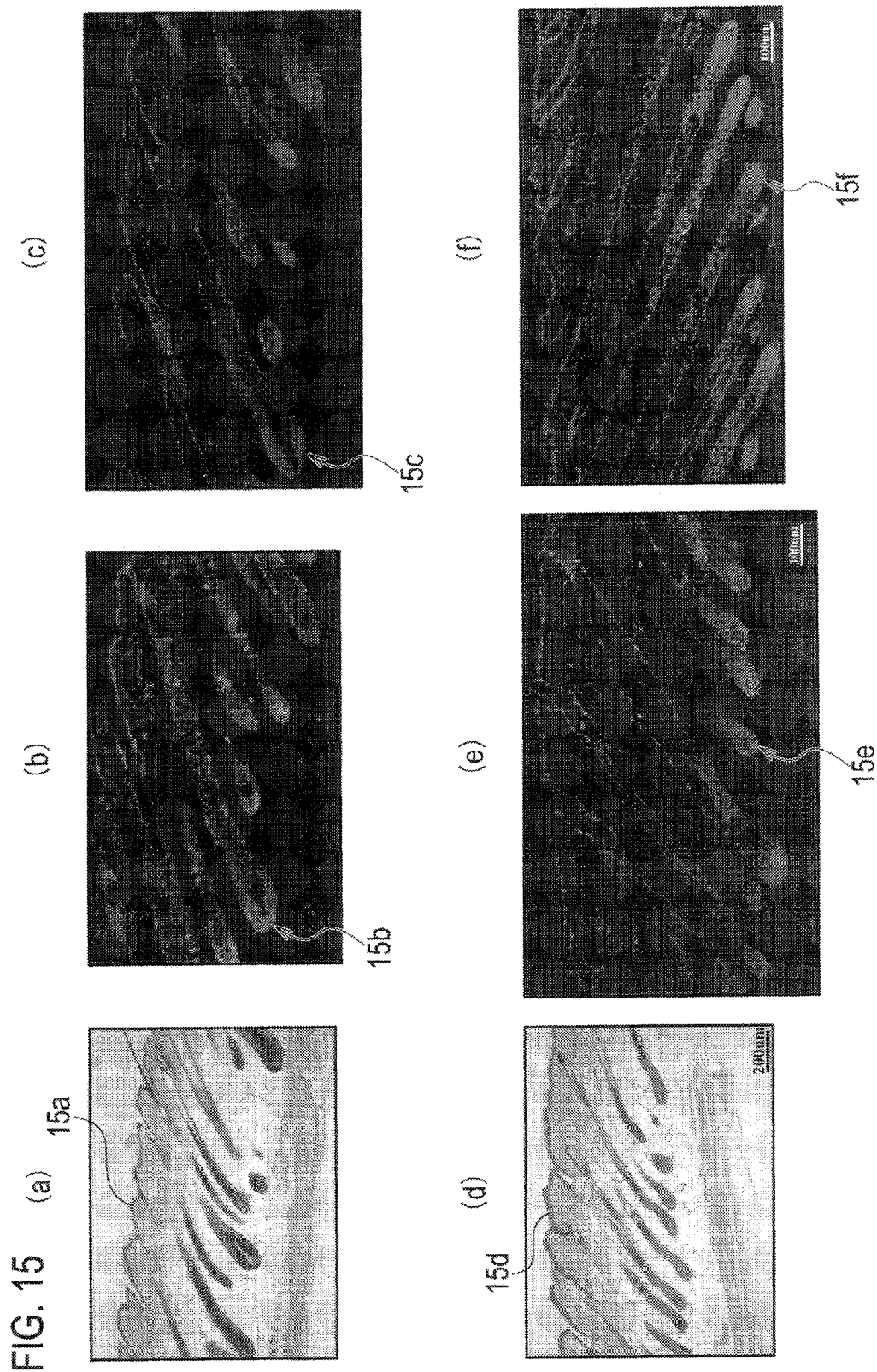
FIG. 15(a) is a micrograph illustrating a result of HE staining of control mouse skin.
FIG. 15(b) is a micrograph illustrating a result for control mouse skin in the case of using an anti-BrdU antibody.
FIG. 15(c) is a micrograph illustrating a result for control mouse skin in the case of using an anti-ssDNA antibody.
FIG. 15(d) is a micrograph illustrating a result of HE staining of control mouse skin five days after irradiation.
FIG. 15(e) is a micrograph illustrating a result for control mouse skin five days after irradiation in the case of using an anti-BrdU antibody.
FIG. 15(f) is a micrograph illustrating a result for control mouse skin five days after irradiation in the case of using an anti-ssDNA antibody.

Similarly, FIGS. 14(a) to 14(f) illustrate microscopic observation results at 10 magnifications three days after irradiation. FIGS. 14(a) to 14(c) illustrate observations of mouse skin of the control group not irradiated with light. FIG. 14(a) illustrates a result of HE staining, FIG. 14(b) illustrates a result in the case of using an anti-BrdU antibody, and FIG. 14(c) illustrates a result in the case of using an anti-ssDNA antibody. FIGS. 14(d) to 14(e) illustrate observations of mouse skin irradiated with light. FIG. 14(d) illustrates a result of HE staining, FIG. 14(e) illustrates a result using an anti-BrdU antibody, and FIG. 14(f) illustrates a result in the case f using an anti-ssDNA antibody. Similarly, FIGS. 15(a) to 15(f) illustrate microscopic observation results at 10 magnifications five days after irradiation. FIGS. 15(a) to 15(c) illustrate observations of mouse skin of the control group not irradiated with light. FIG. 15(a) illustrates a result of HE staining, FIG. 15(b) illustrates a result in the case of using an anti-BrdU antibody, and FIG. 15(c) illustrates a result in the case of using an anti-ssDNA antibody. FIGS. 15(d) to 15(e) illustrate observations of mouse skin irradiated with light. FIG. 15(d) illustrates a result of HE staining, FIG. 15(e) illustrates a result in the case of using an anti-BrdU antibody, and FIG. 15(f) illustrates a result in the case of using an anti-ssDNA antibody.

The results of FIGS. 12(a) to 15(f) revealed that melanocytes containing melanin and some of kelatinocytes underwent cell death within about 10 hours after the irradiation and the dead cells were discharged out of the body within several days. Such a result illustrates that light irradiation may increase an apparent anagen phase due to delay of the cell cycle and the like. The hair follicles of the group irradiated with light were smaller than those of the control group. Furthermore, no melanin was observed three days after the irradiation in the follicles of the group irradiated with light.

Figure 17:
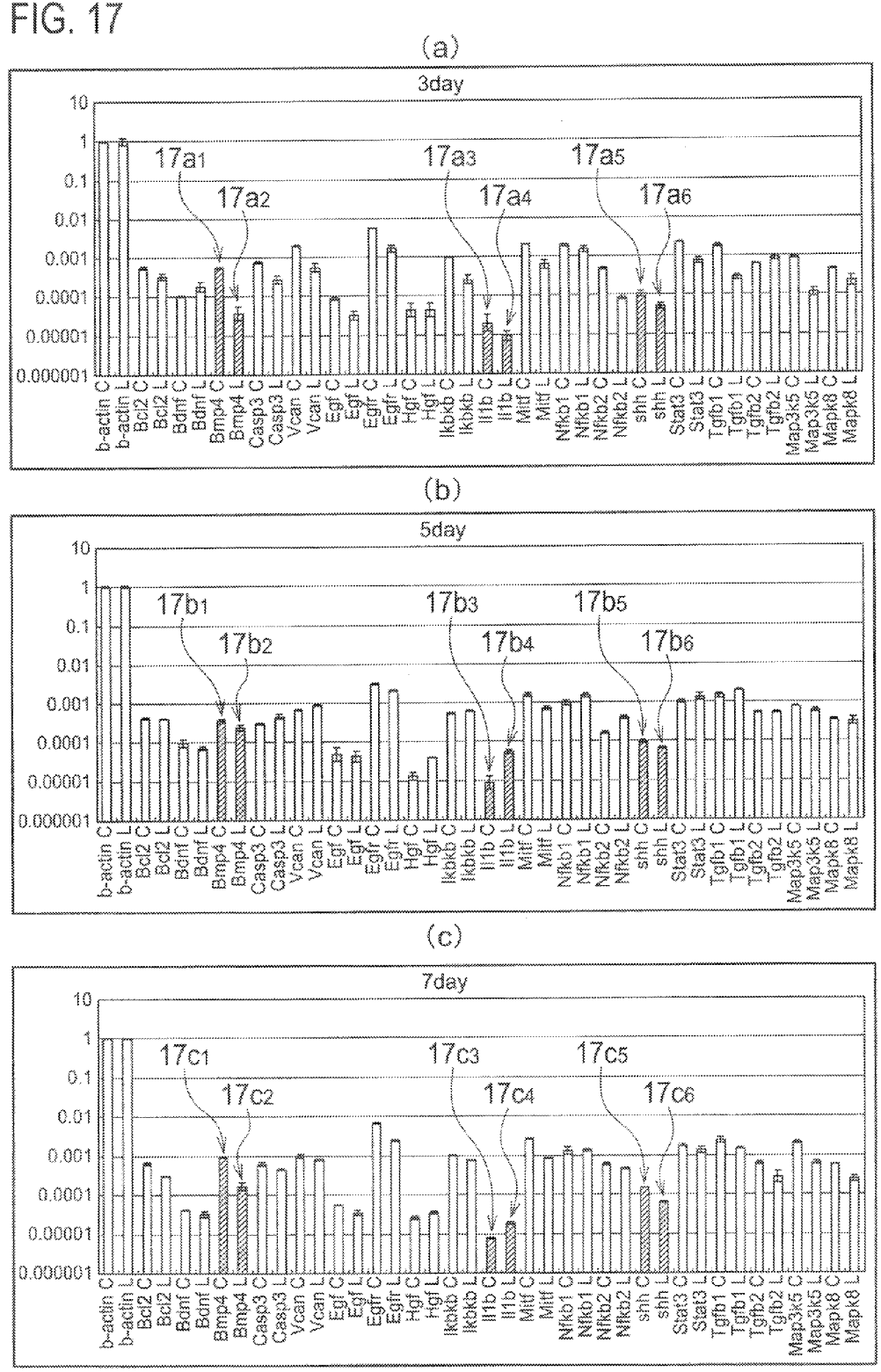
FIG. 17(a) is a diagram illustrating a result of real time PCR three days after irradiation.
FIG. 17(b) is a diagram illustrating a result of real time PCR five days after irradiation.
FIG. 17(c) is a diagram illustrating a result of real time PCR seven days after irradiation.

Next, the results of real time PCR are illustrated. FIGS. 16(a) to 16(c) and FIGS. 17(a) to 17(c) illustrate results two hours, 12 hours, one day, three days, five days, and seven days after irradiation, respectively. In each of the figures, left bars with C mean the results of the control group, and right bars with L mean the results of the group irradiated with light. Based on the FIGS. 16(a) to 16(c) and FIGS. 17(a) to 17(c), there were changes in expression of, especially, Il1b (Interleukin 1β) shh, and Bmp4. The expression of Il1b was increased in the skins irradiated with light, and it is therefore considered that inflammation occurred. Moreover, expression of shh and Bmp4 was reduced in the group irradiated with light. There were differences between the PCR results of the irradiated group and the control group seven days after the irradiation as illustrated in FIG. 17(c). This is considered to be because hair of the control group was growing while hair of the irradiated group was prevented from growing.

Example 2

Next, the circuit design was changed to set the capacitance of the main capacitor to 800 µF, which was twice that of Example 1. Moreover, a long pass filter (OG570, SCHOTT) was provided at the front of the lens. The intensity of emitted light was doubled by doubling the capacitance of the capacitor, and the short-wavelength components were cut off by the filter. Accordingly, 550 to 1200 nm wavelength light was distributed as pulses having a full width at half maximum of 1200 µs so as to have energy intensity of 0.2 to 0.3 J/cm² at a distance of 5 mm from the front surface of the lens.

FIG. 18(a) illustrates an irradiation spectrum 18A of Example 1, an irradiation spectrum 18B of Example 2, and melanin absorptance 18C. In the irradiation spectrum 18B of Example 2, wavelengths of 550 nm or shorter were cut off. Moreover, by doubling the capacitance of the capacitor, the irradiation energy was substantially doubled at a wavelength of 640 nm, for example.

Next, FIG. 18(b) illustrates a diagram comparing energies (graph areas) absorbed by melanin in Examples 1 and 2, which were calculated by multiplying the irradiation spectra of Examples 1 and 2 by the absorptance of melanin. 18D and 18E indicate the melanin absorbing energies of Examples 1 and 2, respectively. The melanin absorbing energy in Example 2 was larger than that of Example 1.

FIG. 19(a) illustrates an irradiation spectrum 19A of Example 1, an irradiation spectrum 19B of Example 2, the melanin absorptance 19C, and eumelanin absorptance 19D. FIG. 19(b) illustrates a diagram comparing energies (graph areas) absorbed by melanin and eumelanin in Examples 1 and 2, which were calculated by multiplying the irradiation spectra of Examples 1 and 2 by each of the melanin absorptance and eumelanin absorptance. 19E and 19F indicate the melanin absorbing energies of Examples 1 and 2, respectively. 19G and 19H indicate the eumelanin absorbing energies of Examples 1 and 2, respectively. Comparing the melanin absorptance and eumelanin absorptance 19C and 19D, the eumelanin absorptance 19D provides a flatter absorption characteristic than that of the melanin absorptance 19C.

Figure 20:
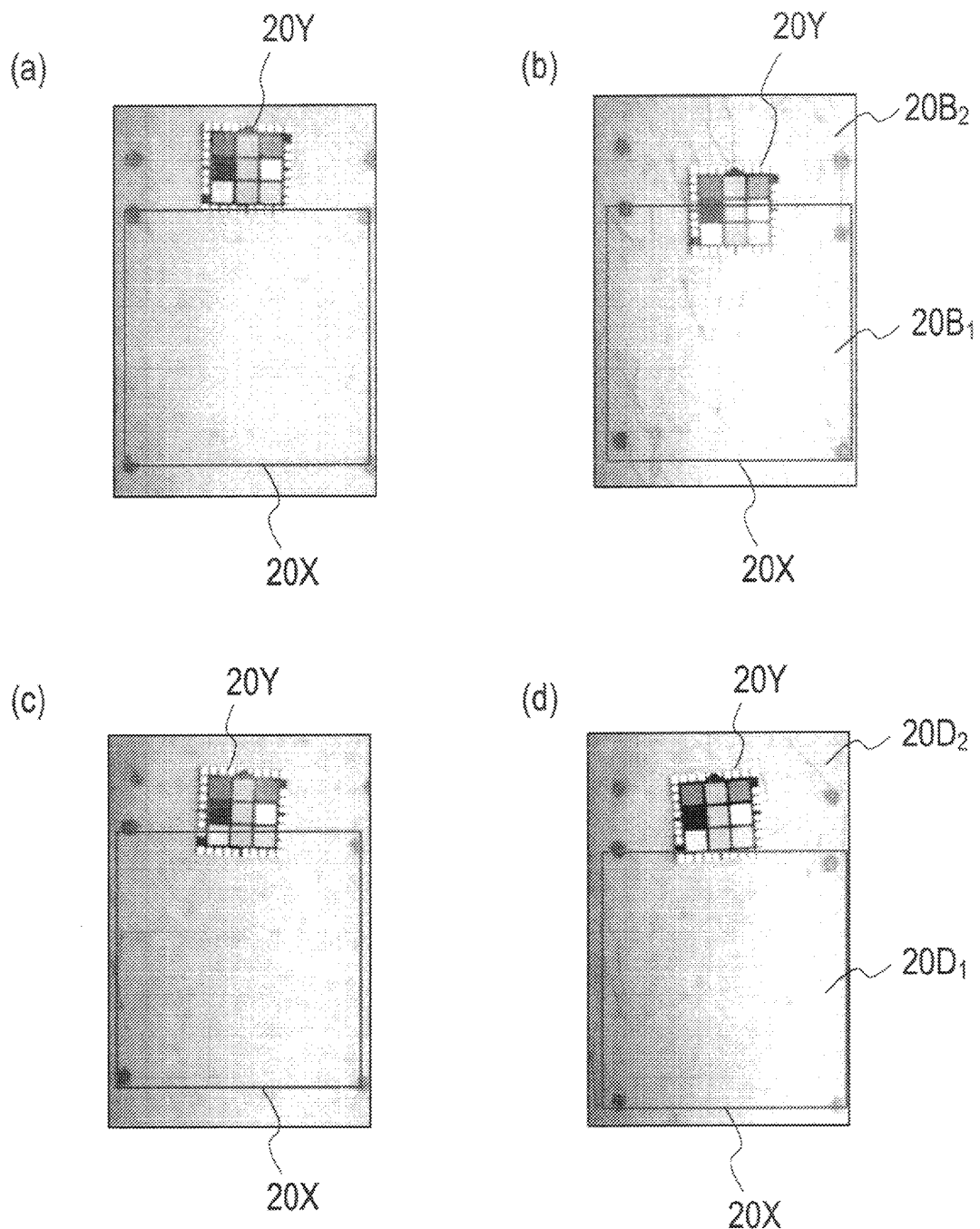
FIG. 20(a) is a view illustrating a skin surface below a knee of a human immediately after hair removal in Example 1.
FIG. 20(b) is a view illustrating a skin surface below a knee of a human one month after hair removal in Example 1.
FIG. 20(c) is a view illustrating a skin surface below a knee of a human immediately after hair removal in Example 2.
FIG. 20(d) is a view illustrating a skin surface below a knee of a human one month after hair removal in Example 2.

Next, FIG. 20(b) illustrates a skin surface below a knee of a human immediately after hair removal in Example 1, and FIG. 20(b) illustrates the skin surface below the knee of the human one month after the hair removal of Example 1. FIG. 20(c) illustrates a skin surface below a knee of a human immediately after hair removal in Example 2, and FIG. 20(d) illustrates the skin surface below the knee of the human one month after the hair removal of Example 2. The irradiation was continued for ten days and was not performed for 20 days.

In each drawing, 20X indicates an irradiation range, and 20Y indicates a color chart. As illustrated in FIG. 20(b), in Example 1, hair was grown in an irradiated part 20B1 although the growth thereof was slower than that in a non-irradiated part 20B2. On the other hand, as illustrated in FIG. 20(d), the hair growth was inhibited in Example 2 more than Example 1, and hair was hardly grown in an irradiated part 20D1. As described above, the hair reducing effect of Example 2 was higher than that of Example 1.

The cut-off wavelength was changed according to the type of melanin contained in the skin to control energy so that the irradiance at the skin surface was constant or the spectrum areas illustrated in FIGS. 18 and 19 were constant. When the irradiance is constant, the total intensity of energy projected on the skin surface is constant, and amount of heat at the skin surface will not increase. If the content of eumelanin is high among the melanins contained in the skin, the irradiation energy in a long-wavelength band with high penetration depth is increased to increase the absorption deep in the skin. On the other hand, if the content of pheomelanin is high among the melanins contained in the skin, the absorptance in the long wavelength band is low. Accordingly, the irradiation light is configured so as to include shorter wavelength components than that in the case where the skin contains a lot of eumelanin, and at least the absorption peak of blood vessels is cut off, thus increasing the absorption efficiency deep in the skin. Moreover, controlling the intensity of light according to the content of melanin in the skin makes is possible to efficiently remove and reduce hair with less side effects.

Hereinabove, the embodiment of the present invention is described. However, it should not be understood that the description and drawings constituting a part of the disclosure of the aforementioned embodiment limits the present invention. Based on this disclosure, skilled in the art will understand various substitutions, examples, and operation techniques.

The whole contents of Japanese Patent Application No. 2009-002762 (Filed Date: Jan. 8, 2009) are incorporated herein.

INDUSTRIAL APPLICABILITY

By providing the light source giving pulses of light in a wavelength range from 400 to 1200 nm and a light guide distributing the pulses of light given from the light source with energy intensity of 0.2 to 10 J/cm² at a predetermined distance from the light outgoing surface, it is possible to provide a light irradiation device capable of easily removing and reducing hair with low power light without no burden on skin.

Reference Signs List

| | |
|---|---|
| 1 | light irradiation device |
| 2 | body |
| 2a | attachment operation portion |
| 2b | power switch |
| 2c | irradiation side end |
| 2d | unit attachment portion |
| 3 | body cover |
| 4 | irradiation unit |
| 4a | attachment protrusion |
| 5 | lens |
| 6 | light orientation controller |
| 6a | emission portion |
| 6a1 | partition member |
| 6a2 | compartment |
| 6b | light shielding portion |
| 7 | after irradiation |
| 8 | lamp casing |
| 9 | light source |
| 10 | reflector |
| 10a | insertion hole |
| 11 | circuit unit |
| 12 | connector |
| 13 | circuit printed board |
| 14 | elastic member |
| 15 | fixture |
| 16 | base |
| 22 | charge controller |
| 23 | capacitor charger |
| 24 | flash controller |
| 25 | peripheral circuit |
| 31 | cover member |
| 32 | cover side engagement portion |
| 33 | body side connector |
| 34 | body side engagement portion |
| 42 | irradiation port |
| 45 | recess |

The invention claimed is:

1. A light irradiation device, comprising:
a light source giving pulses of light in a wavelength range from 400 to 1200 nm; and
a light guide distributing the pulses of light given from the light source in energy intensity of 0.2 to 10 J/cm2 at a predetermined distance from an outgoing surface,
wherein the light guide includes a light orientation controller adjusting the pulses of light from the light source,
wherein the light irradiation device cuts off a wavelength range using a filter, and
wherein the light orientation controller includes a light shielding portion made of an opaque material not transmitting light and an emission portion provided at a substantially rectangular open end of the light shielding portion, and the emission portion is partitioned by a plurality of partition members into a plurality of compartments arranged side by side so as to equalize the intensity of light at a predetermined distance from the outgoing surface.

2. The light irradiation device according to claim 1, wherein the light source gives the pulses of the light in a wavelength range from 550 to 1200 nm.

3. The light irradiation device according to claim 1, further comprising:
an accommodation member accommodating the light source and the light guide, the accommodation member including a grip.

* * * * *